United States Patent
Cowden et al.

(10) Patent No.: US 7,648,966 B2
(45) Date of Patent: Jan. 19, 2010

(54) MANNOSE-6-PHOSPHONATE COMPOUNDS FOR THE TREATMENT OF INFLAMMATORY DISEASES

(75) Inventors: William Butler Cowden, Kambah (AU); Gavin James Bartell, Conder (AU); Bart Michael Eschler, Giralang (AU); Darren Ray March, Banks (AU); Alan Robertson, Warrawee (AU)

(73) Assignee: Pharmaxis Pty Limited, French Forest NSW (AU)

( * ) Notice: Subject to any disclaimer, the term of this patent is extended or adjusted under 35 U.S.C. 154(b) by 385 days.

(21) Appl. No.: 10/557,773

(22) PCT Filed: May 20, 2004

(86) PCT No.: PCT/US2004/015876

§ 371 (c)(1),
(2), (4) Date: Nov. 21, 2005

(87) PCT Pub. No.: WO2004/104015

PCT Pub. Date: Dec. 2, 2004

(65) Prior Publication Data

US 2007/0082850 A1    Apr. 12, 2007

Related U.S. Application Data

(60) Provisional application No. 60/471,716, filed on May 20, 2003.

(51) Int. Cl.
*A61K 31/70* (2006.01)
*A61K 31/7028* (2006.01)
(52) U.S. Cl. .............................. 514/25; 514/27; 536/4.1
(58) Field of Classification Search ................... 514/25, 514/27; 536/4.1
See application file for complete search history.

(56) References Cited

U.S. PATENT DOCUMENTS 6,140,307 A    10/2000    Ferguson et al.

FOREIGN PATENT DOCUMENTS

| AU | 41866/97 | 4/1998 |
| WO | WO 85/05031 | * 11/1985 |
| WO | WO 02/04472 | 1/2002 |

OTHER PUBLICATIONS

Vidil et al. (European Journal of Organic Chemistry (1999), (2) 447-450).*
Barragan et al. (Chemical Communications (2001), (1), 85-86).*
Barragan et al., A Mannose-6-Phosphonate-Cholesterylamine Conjugate As A Specific Molecular Adhesive Linking Cancer Cells With Vesicles, Chem. Comm., 2001, pp. 85-86, XP002301443.
Vidil et al., Synthese De Manose 6-Phosphonates, Analogues Isosteres Due Mannose 6-Phosphate, vol. 158, 2000, pp. 125-139, XP009038355.

* cited by examiner

*Primary Examiner*—Shaojia Anna Jiang
*Assistant Examiner*—Michael C Henry
(74) *Attorney, Agent, or Firm*—Venable LLP; Ann S. Hobbs

(57) ABSTRACT

Novel phosphotetrahydropyran compounds that mimic mannose-6-phosphate but that are more resistant to phosphatases and mannosidases, and pharmaceutical compositions thereof, are disclosed. These compounds and compositions inhibit T lymphocyte migration from blood to tissues or to other extravascular sites. By inhibiting such migration, these compounds are useful for treating diseases or disorders that are mediated at least in part by such T lymphocyte migration. Such diseases and disorders include rheumatoid arthritis, multiple sclerosis, acute disseminated encephalomyelitis, psoriasis, inflammatory bowel disease, T cell-mediated dermatitis, stromal keratitis, uveitis, thyroiditis, sialitis and type I diabetes.

20 Claims, 1 Drawing Sheet

MANNOSE-6-PHOSPHONATE COMPOUNDS FOR THE TREATMENT OF INFLAMMATORY DISEASES

BACKGROUND OF THE INVENTION

1. Field of the Invention

The present invention relates generally to novel phosphotetrahydropyran compounds, primarily derivatives of mannose-6-phosphate, and their use in treating diseases or disorders that are mediated at least in part by T lymphocyte emigration from blood to tissues. In particular, the present invention relates to the use of these compounds and pharmaceutical compositions comprising them to treat T lymphocyte mediated inflammatory and autoimmune diseases in animals and man.

2. Description of the Background Art

The adaptive immune response of mammals may be viewed as being divided into two arms: antibody (or humoral) and cell-mediated immune responses. Different classes of lymphocytes play key role in these two type of responses. Antibody responses are generated by antibody-producing B lymphocytes (or B cells) which differentiate into plasma cells, while cell-mediated immune responses are mediated by T cells, such as cytotoxic T lymphocytes (CTL) which specifically recognize and kill antigen-bearing target cells, such as infected cells or tumor cells. These "effector" T cells commonly recognized their target antigens in the context of major histocompatibility complex (MHC) proteins, usually MHC class I proteins. Both classes of immune responses usually depend upon the action of another set of T lymphocytes, T helper cells, which also recognize antigenic epitopes presented in the context of major histocompatibility complex (MHC) proteins, usually MHC class II proteins. The processes involved in the generation and manifestation of these responses and the roles played by the various classes of lymphocytes in infection are well understood. For a more detailed explication of the foregoing and other description in this section, see immunology textbooks such as Abbas, A K et al., eds., *Cellular and Molecular Immunology* (4th Ed.), W.B. Saunders Co., Philadelphia, 2000, Janeway, C A et al., eds., *Immunobiology*, 5th ed., Garland Publishing Co., New York, 2001; Roitt, I et al., eds, *Immunology*, $5^{th}$ ed., C.V. Mosby Co., St. Louis, Mo. (2001); Klein, J et al., *Immunology*, $2^{nd}$ edition, Blackwell Scientific Publications, Inc., Cambridge, Mass., (1997).

T cells are believed to engage in a process termed "immunological surveillance" which they execute by continuously circulating (recirculating) throughout the body. Recirculation involves migration of T cells from lymph nodes (LN) into the blood stream via the efferent lymphatic ducts and then re-entry into LN from the blood via post capillary venules. T cells also exit the circulation by crossing capillary walls and entering tissues, moving through the tissues, and entering afferent lymphatic vessels draining these tissues, and finally making their way via these lymphatics to local draining LNs which are positioned around the body.

If, during this sojourn through the tissues, T cells encounter an antigen that they recognize specifically, via their clonally expressed T cell receptors (TCR), and to which these cells are programmed to respond, the T cells are activated, leading to a state of cell-mediated immunity. Thus, when recognizing and responding to an infectious agent or other foreign antigen, T cells generate responses that ultimately result in destruction and clearance of the pathogen. In some cases, however, the T cell response may not be controlled optimally and therefore become excessive, resulting in collateral damage to normal tissues in the vicinity of the infectious (or other foreign) agent. In other cases, T cells initiate an inappropriate immune response directed to normal tissue components or "self-antigens." Irrespective of the mechanism of these "normal," aberrant or dysregulated responses, when they become clinically apparent, the resulting disease or disorder is often termed an "autoimmune disease." The cell and tissue damage is commonly referred to as "immunopathology." Many pathological disorders of humans have been attributed to autoreactive T lymphocytes and the inflammatory responses they induce. See, Gallin, J et al. (eds), *Inflammation: Basic Principles and Clinical Correlates*, $3^{rd}$ Edition, Lippincott Williams & Wilkins, 1999. Included-among these immunopathological maladies a number of well-known autoimmune diseases (see, for example, A. N. Theofilopoulos et al. (eds), $2^{nd}$ edition, *The Molecular Pathology of Autoimmune Diseases*, Taylor & Francis, 2002)). Examples of these are multiple sclerosis (MS), rheumatoid arthritis (RA), inflammatory bowel disease (IBD), acute disseminated encephalomyelitis (ADE) and insulin-dependent diabetes mellitus (IDDM, also Type I diabetes). Psoriasis too is a T cell-mediated inflammatory disease of the skin (Bos, J D et al., *Immunol. Today* 20:40-46 (1999)).

Approaches and agents for treatment or prevention of immunopathology and autoimmune diseases, developed over decades, target many and varied facets of the immune and inflammatory processes described above. Though some agents are specific to particular antigens, the vast majority have been nonspecific (see textbook references, supra). Although current approaches have met with varying degrees of success, many carry with them multiple undesirable side effects and risks.

Several investigators have targeted various steps in the T cell migration/extravasation process as an approach to suppressing some of the autoimmune disorders noted above. Several studies by Israeli investigators are described first. Naparstek, Y et al., *Nature* 310:241-244 (1984) discussed earlier studies of lines of activated T lymphocytes specifically sensitized to the central nervous system (CNS) antigen, myelin basic protein (MBP); upon intravenous inoculation into syngeneic rats, these T cells penetrated blood vessels, accumulated in the CNS parenchyma and caused the inflammatory/immune sequelae manifested as experimental autoimmune encephalomyelitis (EAE), a well-recognized animal model of human MS. These authors studied interactions of activated anti-MBP T lymphocytes with the basement membrane-like extracellular matrix (ECM) produced by vascular endothelial cells. They found that activated, but not resting T lymphocytes, produced an endoglycosidase (heparanase) enzyme capable of degrading heparan sulfate side chains of the proteoglycan scaffold of the ECM and responded to MBP presented by the ECM by enhanced elaboration of this enzyme. These results suggested that tissue-specific antigens on blood vessel walls could direct lymphocyte "homing" by activating enzymes that facilitate penetration of the subendothelial basal lamina. Following up the above study, Lider, O et al., *J. Clin. Invest.* 83:752-756 (1989), found that administration of low dose heparin to mice inhibited lymphocyte traffic and delayed-type hypersensitivity (DTH) reactions ('classic' cell-mediated immune responses). Treatment with commercial or chemically modified heparins at relatively low doses once daily (e.g., 5 µg/mouse; 20 µg/rat) led to inhibition of allograft rejection and two experimental auto-immune diseases (EAE and adjuvant arthritis). The ability of chemically modified heparins to inhibit the migration stages of the immune reaction was associated with their ability to inhibit expression of T lymphocyte heparanase. Importantly, there was no relationship of this T cell inhibitory effect with the heparins' anticoagulant activity. Thus appropriate doses of heparins, even if devoid of anticoagulant activity, could effectively regulate or inhibit undesired T cell migration involved in autoimmune diseases.

Subsequently, Lider, O et al., *Eur. J. Immunol.* 20:493-499 (1990), reported studies of the effects in vitro and in vivo of the heparanase inhibitor, heparin, on the expression of T lymphocyte heparanase and on the ability of T lymphocytes to mediate a DTH reaction. T cell heparanase activity could be induced in vivo by immunizing mice with an antigen or in vitro by activating T lymphocytes polyclonally with a mitogen. Again, low doses of heparin inhibited the expression of heparanase induced either way. The same doses of heparin that inhibited expression of heparanase also inhibited the ability of LN T cells to migrate to a site of antigen and adoptively produce a DTH reaction. These findings further supported the notion of modulating cell-mediated immunity using heparin which would inhibit expression of T lymphocyte heparanase expression and cell migration. Vlodavsky, I et al. (*Invas. Metas.* 12:112-127 (1992), further discussed the importance of heparanase in the interactions of T lymphocytes (as well as B lymphocytes, platelets, granulocytes, macrophages and mast cells) with the subendothelial ECM, due to degradation of heparan sulfate by this enzyme. The enzyme is released from intracellular compartments (i.e., lysosomes, specific granules) in response to various activation signals (e.g., antigens, mitogens), explaining heparanase's role in inflammation and cellular immunity. Of interest was the fact that various tumor cells expressed and secreted heparanase in a constitutive manner, which was correlated with their metastatic potential. Thus, utilizing a shared mechanism, T cells and other normal leukocytic cells on the one hand, and metastatic tumor cells on the other, which enter the bloodstream, can travel to distant sites and extravasate to the tissue parenchyma there by means of this cellular heparanase enzyme.

There is clearly a need in the art for new inhibitors of undesired cellular migration, particularly T cell migration, that can be exploited in the treatment of various diseases or disorders associated with inflammation and immune responses that involve such cellular migration as a step in the pathophysiology.

As is described below, a cell surface receptor for mannose-6-phosphate (M6P) on T lymphocytes appears to play a role in their extravasation in vivo. The background to that observation is as follows. Recirculating lymphocytes initiate extravasation from the blood stream by binding to specialized high endothelial venules (HEV) within peripheral LNs and other secondary lymphoid organs. Stoolman, L M et al. (*J. Cell Biol.* 99:1535-1540 (1984)) reported selective inhibition of lymphocyte attachment to HEV by M6P and related carbohydrates. Yednock, T A et al. (*J. Cell Biol.* 104: 713-723, 725-731 (1987)) employed a cell-surface probe—fluorescent beads derivatized with 'PPME", an M6P-rich polysaccharide—to directly identify a carbohydrate-binding receptor on lymphocytes surfaces. Lymphocyte attachment to PPME beads mimicked the interaction of lymphocytes with LN HEV: both interactions were selectively inhibited by the same panel of structurally related carbohydrates, were calcium-dependent, and were sensitive to mild trypsin treatment of lymphocytes. Thymocytes (and certain thymic lymphoma cell lines) which bind very weakly to HEV, also bound poorly to PPME beads. The authors concluded that a carbohydrate-binding receptor on lymphocytes, detected by these PPME beads, is involved in lymphocyte attachment to LN HEV.

The initiation of lymphocyte extravasation employs a family of cell adhesion molecules called homing receptors that mediate lymphocyte attachment to HEV within the lymphatic tissues. A putative homing receptor was identified by the monoclonal antibody (mAb), MEL-14, which recognized an 80-90 kDa glycoprotein on the surface of mouse lymphocytes and blocked their attachment to LN HEV. The authors examined the relationship between the carbohydrate-binding receptor and the putative homing receptor identified by MEL-14 and found that: MEL-14 completely and selectively blocked the activity of the lymphocyte carbohydrate-binding receptor; the ability of six lymphoma cell lines to bind PPME beads correlated with cell-surface expression of the MEL-14 antigen, as well as LN HEV-binding activity; selection of lymphoma variants that bind to PPME-beads produced highly correlated and selective changes in MEL-14 antigen expression. The authors concluded that the carbohydrate-binding receptor on lymphocytes and the MEL-14 antigen, which have been independently implicated as receptors involved in LN-specific HEV attachment, are very closely related, if not identical, molecules.

A group of investigators in Canberra, Australia, that included one of the present inventors (Cowden) studied the ability of phosphosugars to inhibit CNS inflammation (Willenborg, D O et al., *FASEB J.* 3:1968-1971 (1989)). They found that adoptively transferred EAE was inhibited by various phosphosugars, particularly M6P. The authors speculated that the sugar specificity may be due to depletion of lymphocyte cell-surface lysosomal enzymes that are essential for the passage of lymphocytes across the vascular endothelium and entry into the CNS parenchyma. A later study by the same group (Willenborg et al. *Immunol. Cell Biol.* 70:369-377 (1992)) showed that development of joint inflammation in a model of adoptively transferred arthritis in rats was also inhibited by treatment with M6P and by the alkaloid inhibitor of α-glucosidase, castanospermine (CS). M6P was effective at a dose of 25 mg/kg per day delivered via mini-osmotic pumps implanted either subcutaneously (sc) or intraperitoneally. CS was given orally in the drinking water (actual dose ~60-65 mg/kg per day), which treatment greatly reduced inflammatory infiltrates in the synovium and surrounding tissue. CS also inhibited disease progression when treatment was commenced after the onset of symptoms. The authors speculated that the mechanism(s) of action included inhibition of the passage of leucocytes through vascular subendothelial basement membranes by inhibiting the function or expression of leucocyte cell surface-bound enzymes that are essential for such migration.

In another study by the same group (Bartlett, M R et al., *Immunol. Cell Biol.* 72:367-374 (1994)), M6P, CS and some sulfated polysaccharides (SPS) were tested in murine models of allograft rejection and elicitation of peritoneal exudates. CS, M6P and the SPS, fucoidin (or fucoidin), partially inhibited rejection of permanently accepted thyroid allografts (induced by the i.p. injection of donor strain allogeneic spleen cells). Elicitation of inflammatory exudates by thioglycollate was inhibited by CS, M6P and fucoidin with sustained leukopenia being induced by CS. In contrast, CS and fucoidin, but not M6P, inhibited antigen-elicited peritoneal exudates. The authors claimed that, while these results suggested that CS, M6P and the fucoidin exhibited subtle differences in their anti-inflammatory activity, the mechanism of inhibition was at the level of leukocyte extravasation.

The Canberra group directly tested the hypothesis that heparin, M6P and CS mediate their anti-inflammatory effects by inhibiting the passage of leukocytes through the subendothelial basement membrane (SBM) (Bartlett et al., *J. Leukoc. Biol.* 57:207-213 (1995)). These three compounds were examined for their ability to prevent the in vitro degradation of a $^{35}SO_4$-labeled ECM by neutrophils, lymphocytes, endothelial cells (ECs), and platelets. While all three compounds inhibited ECM degradation, M6P and CS were cell-type specific in their effects. Heparin inhibited the heparanase activity of all cell types examined, confirming the results of previous studies (discussed above). M6P selectively inhibited lymphocyte heparanase but not that of platelets, neutrophils, or ECs. CS selectively inhibited induced EC heparanase and sulfatase activity but did not affect the constitutive expression of these degradative enzymes by unstimulated ECs. The results were said to support the view that leukocytes markedly differ in the mechanisms by which they degrade SBM/ECM to enable extravasation.

In a review article (Parish, C R et al. *Immunol. Cell Biol.* 76(1):104-13 (1998)), the Canberra group discussed the inadequacy of current anti-inflammatory drugs in the treatment of MS and other inflammatory diseases because (a) disease progression was not arrested and (b) undesirable side effects posed problems. They discussed their decade-long (see studies described above) development of novel drugs that could interfere with the entry of leucocytes into inflammatory sites by inhibiting their passage through the SBM. An important point emerging from their research was that breach of the SBM is a cooperative process, involving activation-induced and cytokine-induced degradative enzymes contributed by leucocytes, endothelial cells and platelets. This document described the properties of three separate classes of anti-inflammatory compounds: (1) phosphosugars, (2) sulfated polysaccharides/oligosaccharides and (3) CS, all of which inhibit the passage of leukocytes through SBM. Each "drug" type appears to prevent SBM degradation by a different mechanism. Sulfated polysaccharides/oligosaccharides mediate their anti-inflammatory effect by inhibiting the endoglycosidase, heparanase, which plays a key role in the solubilization of SBM by invading leucocytes. Phosphosugars probably inhibit inflammation by displacing lysosomal enzymes involved in SBM degradation from cell surface M6P receptors. This mechanism—expression of degradative enzymes on the cell surface—was particularly evident in activated T lymphocytes. For reasons which were said to be unclear, CS specifically inhibits SBM degradation by ECs, which results in a characteristic perivascular arrest of leucocytes in inflammatory sites. The review concluded that inhibitors of SBM degradation represent viable anti-inflammatory agents for future development.

A more recent publication by the Canberra group (Hindmarsh, E J et al., *Immunol Cell Biol* 79:436-43 (2001)) evaluated the antiinflammatory action of M6P, notably in the inhibition of EAE and adjuvant-induced arthritis in rats. It was proposed that M6P exerted its anti-inflammatory effect by displacing lysosomal enzymes (which are involved in T cell extravasation into inflammatory sites) from the 300 kDa M6P receptor (=MPR-300) on the T cell surface. The authors hypothesized that MPR-300 would be selectively expressed on the surface of activated T cells, as T cell entry into the CNS in EAE depends on the activated state of the cells. They therefore examined (a) correlation between cell surface expression of MPR-300 on T cells and their state of activation, and (b) whether T cells in inflammatory sites expressed the receptor. Flow cytometric studies showed MPR-300 was absent from the surface of unstimulated rat T cells isolated from peripheral blood and lymphoid tissues, and from T cells resident within the peritoneal cavity. In contrast, MPR-300 was expressed on activated T cells derived from an inflammatory peritoneal exudate. In vitro studies demonstrated transient expression of MPR-300 on the surface of splenic T cells following stimulation with Con A. MPR-300 was also induced on T cell lines by antigen stimulation. The authors concluded that T cells in inflammatory sites express MPR-300 on their surface and that activation of these cells induces cell surface expression of this receptor. Such findings were said to be consistent with the notion that cell surface MPR-300 is required for the entry of T cells into inflammatory sites.

A commonly owned PCT application published as WO/0204472, exploited the foregoing observations by the Canberra group and described various novel M6P derivative compounds and their use in treating diseases that are dependent upon T lymphocyte migration.

As a next step in the development of effective inhibitors of T cell migration and extravasation, the present inventors have discovered yet other, improved phosphotetrahydropyran compounds (distinct from those in WO/0204472) that are defined by Formula I, below. The compounds of this invention are more resistant to endogenous mannosidase and phosphatase enzymes, are effective inhibitors of T lymphocytes migration from the blood into tissues and are thus useful additions to our armamentarium of treatments for autoimmune diseases and, in general, for any disease or disorder that involves such T lymphocyte migration in its pathogenesis.

SUMMARY OF THE INVENTION

The present inventors have discovered a series of derivatives of mannose-6-phosphate (M6P) that are resistant to phosphatase and mannosidase enzymes.

The present invention provides a tetrahydropyran compound of formula (I):

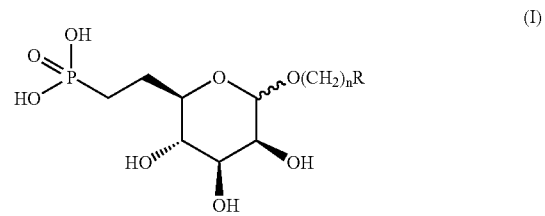

wherein n is an integer from 0 to 3, the —O(CH$_2$)$_n$R group is in an axial or equatorial "position", and R is (i) an optionally substituted aryl or heteroaryl, for example an aralkyl or heteroaralkyl, or (ii) an optionally substituted lower alkyl, for example, a di-substituted butyl group wherein C2 and C4 are substituted. Also included are salts, derivatives or prodrugs of the above compound.

In a preferred embodiment of the compound of claim 1, R is an aryl group preferably substituted by one or more substituents selected from the group consisting of halo, alkyl, alkenyl, alkynyl, alkoxy, aryl, acyl, acyloxy carboxy, amido and amino groups. In accordance with the definitions below, the alkyl, alkenyl, alkynyl, alkoxy, aryl, acyl, etc., substituents of the aryl R group are themselves optionally substituted.

Examples of preferred substituents are selected from the group consisting of —CH$_3$, —CH$_2$CH$_3$, —(CH$_2$)$_m$CO$_2$R$^1$, —(CH$_2$)$_m$CH$_2$OR$^2$, —(CH$_2$)$_m$CONHR$^2$, —(CH$_2$)$_m$NHR$^2$, —(CH$_2$)$_m$CONR$^2$R$^3$ and —(CH$_2$)$_m$CONR$^2$R$^3$, wherein m is an integer from 0 to 3; R$^1$ is selected from the group of consisting of H, alkyl and aryl; and R$^2$ and R$^3$ are independently selected from the group consisting of H, alkyl, aryl and acyl.

The present invention includes subgenuses of the compound of claim 1 with various molecules or groups of structures disclaimed. These are listed in the Detailed Description section below.

In another embodiment of the compound of claim 1, R is selected from the group consisting of phenyl; 2-methylphenyl; 2,4-dimethylphenyl; 2,4,6-trimethylphenyl; 2-methyl-4-chlorophenyl; 2-methyl-4-fluorophenyl; aryloxyalkyl; phenoxymethyl; phenoxyethyl; benzyl; phenethyl; 2, 3 or 4-methoxyphenyl; 2, 3 or 4-methylphenyl; 2, 3 or 4-pyridyl; 2, 4 or 5-pyrimidinyl; 2 or 3-thiophenyl; 2,4, or 5-(1,3)-oxazolyl; 2,4 or 5-(1,3)-thiazolyl; 2 or 4-imidazolyl; and 3 or 5-symtriazolyl.

Preferred R groups include 2,4-dimethylphenyl, 2,4,6-trimethylphenyl, 2-methyl,4-chlorophenyl and 2-methyl,4-fluorophenyl, so that the compounds are 1-(2,4-dimethylphenyl)-6-phosphono-mannoside, 1-(2,4,6-trimethylphenyl)-6-phosphono-mannoside, 1-(2-methyl,4-chlorophenyl)-6-phosphono-mannoside, and 1-(2-methyl,4-fluorphenyl)-6-phosphono-mannoside.

A preferred compound in which the R group is a di-substituted lower alkyl group is 2-methyl,4-trifluoromethyl-6-phosphono-mannoside.

Also included is a salt, a derivative or a prodrug of any one of the above compounds.

The present invention also provides a pharmaceutical composition comprising:
(a) any compound as indicated above, including a salt, a derivative or a prodrug; and
(b) a pharmaceutically acceptable carrier, diluent or excipient.

The present invention further provides a method of inhibiting T lymphocyte migration from blood to a tissue or other extravascular site in a subject, comprising administering to the subject an effective amount of (1) a compound as described above, (2) a pharmaceutically acceptable salt derivative or prodrug thereof, or (3) a pharmaceutical composition as described above.

The T lymphocyte migration being inhibited is preferably that associated with a disease or condition in which migrating T lymphocytes mediate an undesired inflammatory or immune response in the tissue or extravascular site.

Also provided is a method of treating an inflammatory or autoimmune disease or condition in a subject in need thereof, comprising administering to the subject an effective amount of (1) a compound as described above, (2) a pharmaceutically acceptable salt derivative or prodrug thereof, or (2) a pharmaceutical composition as described above, wherein the compound, salt, derivative or prodrug results in an inhibition of T lymphocyte migration, primarily T lymphocyte extravasation.

In the above method, the disease or condition may be rheumatoid arthritis, multiple sclerosis, acute disseminated encephalomyelitis, psoriasis, Crohn's disease or other inflammatory bowel diseases, T cell-mediated dermatitis, stromal keratitis, uveitis, thyroiditis, sialitis or type I diabetes.

The present invention is also directed to the use of (1) a compound as described above, or (2) a pharmaceutically acceptable salt derivative or prodrug thereof, in the manufacture of a medicament for the treatment of a disease or condition wherein T lymphocyte migration from blood to a tissue or other extravascular site is a step in the development of the disease or condition.

DESCRIPTION OF THE PREFERRED EMBODIMENTS

Figure 1A:
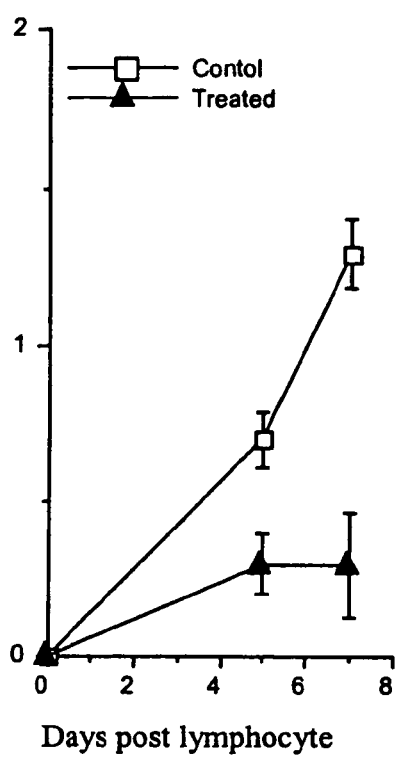
FIGS. 1A and 1B are graphs showing the effect of 1-(2,4-dimethylphenyl)-6-phosphono-mannoside delivered at a dose of 25 mg/kg/day (FIG. 1A) or 37 mg/kg/day (FIG. 1B) on passively transferred adjuvant-induced arthritis in rats. The ordinate shows a disease score (swelling in affected joints in arbitrary units).

The present inventors discovered that certain tetrahydropyrans that are derivatives of M6P are potent inhibitors of T lymphocyte migration and are therefore useful for treating and ameliorating diseases associated with undesired migration of T cells to tissues or other extravascular sites where they mediate immune and inflammatory responses associated with autoimmune diseases. These compounds and their uses are described and exemplified in detail below.

Chemical Structures

The central chemical entity upon which the novel compounds of the present are based is shown in Formula I, below:

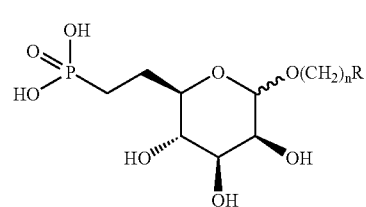

Formula I

In the preferred compounds of this invention, n is an integer, preferably from 0 to 3, the —O(CH$_2$)$_n$R group is in an axial or equatorial position, and the substituent R is an optionally substituted aryl or heteroaryl, for example an aralkyl or heteroaralkyl. This genus of compounds is referred to as the "Formula I compounds". Also included are salts, derivatives and prodrugs of the above Formula I compounds.

The present invention includes various subgenuses of the Formula I compounds, which are listed below:
(1) Formula I, wherein, when n=0, R is not 4-aminophenyl;
(2) Formula I, wherein, when n=0, R is not an amino substituted phenyl;
(3) Formula I, wherein, when n=0, R is not an amino substituted aryl;
(4) Formula I, wherein, R is not 4-aminophenyl;
(5) Formula I, wherein, R is not an amino substituted phenyl; and
(6) Formula I, wherein, R is not an amino substituted aryl;

In another embodiment, the compound of Formula I is one in which R cannot be a phenyl that is substituted with one or more reactive substituents that are characterized by their ability to participate in a nucleophilic attack on a carbonyl to form an amide bond.

In another embodiment, the compound of Formula I is one in which the substituent of the C$_1$ oxygen atom is a group that is less susceptible to the catalytic action of a mannosidase enzyme than is free mannose or a mannoside.

In general, the compounds of Formula I (and the above subgenuses of Formula I) are designed to be less susceptible to the catalytic action of a phosphatase enzyme than is free M6P or another naturally occurring phosphomannoside.

As used herein the term "alkyl", denotes straight chain, branched or cyclic fully saturated hydrocarbon residues. Unless the number of carbon atoms is specified the term preferably refers to C$_{1-6}$ allyl which is also referred to as "lower alkyl." When "alkyl" groups are used in a generic sense, e.g., "propyl," "butyl", "pentyl" and "hexyl," etc., it will be understood that each term may include all isomeric forms (straight, branched or cyclic) thereof. A preferred alkyl is $C_{1-4}$ alkyl; more preferred is $C_{1-3}$ alkyl. Examples of straight chain and branched $C_{1-5}$ alkyl include methyl, ethyl, n-propyl, isopropyl, n-butyl, sec-butyl, tert-butyl, n-pentyl, iso-pentyl, 1,2-dimethyl-propyl, 1,1-dimethylpropyl. Example of cycloalkyl groups are cyclopropyl, cyclopropylmethyl, cyclopropylethyl, cyclobutyl, cyclopentyl, cyclohexyl, etc.

An alkyl group, as defined herein, may be optionally substituted by one or more substituents. Suitable substituents may include: halo (fluoro, chloro, bromo or iodo); haloalkyl (e.g., trifluoromethyl, trichloromethyl); hydroxy; mercapto; phenyl; benzyl; amino; alkylamino; dialkylamino; arylamino; heteroarylamino; alkoxy (e.g., methoxy, ethoxy, butoxy, propoxy phenoxy; benzyloxy, etc.); thio; alkylthio (e.g., methyl thio, ethyl thio); acyl, for example acetyl; acyloxy, e.g., acetoxy; carboxy (—$CO_2H$); carboxyalkyl; carboxyamide (e.g. —CONH-alkyl, —CON(alkyl)$_2$, etc.); carboxyaryl and carboxyamidoaryl (e.g., CONH-aryl, —CON(aryl)$_2$); cyano; or keto (where a $CH_2$ group is replaced by C=O).

The terms "alkoxy" and "acyloxy" refer to alkyl and acyl groups respectively when linked by oxygen.

As used herein the term "alkenyl" denotes groups formed from straight chain, branched or cyclic hydrocarbon residues containing at least one C=C double bond including ethylenically mono-, di- or poly-unsaturated alkyl or cycloalkyl groups as previously defined. Thus, cycloalkenyls are also intended. Unless the number of carbon atoms is specified, alkenyl preferably refers to $C_{2-20}$ alkenyl. More preferred are lower alkenyls ($C_{2-6}$), preferably $C_{2-5}$, more preferably $C_{2-4}$ or $C_{2-3}$. Examples of alkenyl and cycloalkenyl include ethenyl, propenyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl. Preferred alkenyls are straight chain or branched. As defined herein, an alkenyl group may optionally be substituted by the optional substituents described above for substituted alkyls.

As used herein the term "alkynyl" denotes groups formed from straight chain, branched or cyclic hydrocarbon residues containing at least one C≡C triple bond including ethynically mono-, di- or poly-unsaturated alkyl or cycloalkyl groups as previously defined. Unless the number of carbon atoms is specified, the term refers to $C_{2-20}$ alkynyl. More preferred are lower alkynyls ($C_{2-6}$), preferably $C_{2-5}$, more preferably $C_{2-4}$ or $C_{2-3}$ alkynyl. Examples include ethynyl, 1-propynyl, 2-propynyl, butynyl (including isomers), and pentynyl (including isomers). A particularly preferred alkynyl is a $C_{2-6}$ alkynyl. Preferred alkynyls are straight chain or branched alkynyls. As defined herein, an alkynyl may optionally be substituted by the optional substituents described above for alkyl.

The term "acyl" denotes straight chain or branched alkanoyl (C(O)alkyl), alkenoyl (C(O)alkenyl) or alkynoyl (C(O)alkynyl). Preferred alkanoyls are ethanoyl (=acetyl), propanoyl, n-butanoyl, 2-methylpropanoyl, pentanoyl, 2,2-dimethylpropanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl. Examples of alkenoyls are propenoyl, butenoyl, pentenoyl, palmitoyl, oleoyl and lineoyl. The hydrocarbon chain of an acyl may optionally be further substituted by one or more substituents as described above, so that "acyl" is also intended to refer to a substituted acyl.

The term "aryl" denotes a single, polynuclear, conjugated or fused residue of an aromatic hydrocarbon ring system. Examples of aryl are phenyl, biphenyl and naphthyl. An aryl group may be optionally substituted by one or more substituents as herein defined. Accordingly, "aryl" as used herein also refers to a substituted aryl.

The term "heteroaryl" denotes a single, polynuclear, conjugated or fused aromatic heterocyclic ring system, wherein one or more carbon atoms of a cyclic hydrocarbon residue is substituted with a heteroatom to provide a heterocyclic aromatic residue. Where two or more carbon atoms are replaced, the replacing atoms may be two or more of the same heteroatom or two different heteroatoms. Suitable heteroatoms include O, N, S and Se. Examples of heteroaryls include pyridyl, 4-phenylpyridyl, 3-phenylpyridyl, thienyl, furyl, pyrrolyl, indolyl, imidazolyl, oxazolyl, pyridazinyl, pyrazolyl, pyrazinyl, thiazolyl, pyimidinyl, quinolinyl, isoquinolinyl, benzofuranyl, benzothienyl, purinyl, quinazolinyl, phenazinyl, acridinyl, benoxazolyl, benzothiazolyl and the like. As defined herein, a heteroaryl group may be optionally further substituted by one or more substituents as described above.

As used herein the term "aralkyl" denotes the group —Ar—R', wherein Ar is an aryl group and R' is lower alkyl or substituted lower alkyl group. Aryl groups can optionally be substituted at other positions with, e.g., halo, lower alkyl, alkoxy, alkylthio, lower alkenyl, lower alkynyl, amino, amido, carboxyl, hydroxyl, aryl, aryloxy, heterocycle, substituted heterocycle, heteroaryl, substituted heteroaryl, nitro, cyano, thiol, sulfamido and the like. Examples of aralkyl compounds include aromatic compounds having a divalent halomethyl group, hydroxymethyl group, and alkoxymethyl group. Specific examples of aralkyl compounds include monosubstituted 2-, 3- or 4-(chloromethyl)phenyl; disubstituted 2,4- or 2,6-bi(chloromethyl)phenyl; trisubstituted 2,4,6-tri(chloromethyl)phenyl, and other halomethyl and haloalkyl aromatic compounds. Other substituents that can be use in place of the chloromethyls listed above include, for example, hydroxymethyl, or alkoxymethyls (e.g., methyoxymethyl, ethoxymethyl, etc.).

In one preferred embodiment, R in formula I is a substituted aryl group which is substituted by one or more alkyl, carboxy, amido or amino groups, for example, —$CH_3$, —$CH_2CH_3$, —$(CH_2)_mCO_2R^1$, —$(CH_2)_mCH_2OR^2$, —$(CH_2)_m CONHR^2$, —$(CH_2)_mNHR^2$, —$(CH_2)_mCONR^2R_3$ or —$(CH_2)_mCON R^2R^3$ wherein m=0-3, $R^1$ is H, alkyl or aryl, and wherein $R^2$ or $R^3$, independently, is H, alkyl, aryl or acyl.

Other preferred R groups in formula I include: phenyl; 2-methylphenyl; 2,4-dimethylphenyl; 2,4,6-trimethylphenyl; 2-methyl, 4-chlorophenyl; aryloxyalkyl (e.g., phenoxymethyl or phenoxyethyl); benzyl; phenethyl; 2, 3 or 4-methoxyphenyl; 2, 3 or 4-methylphenyl; 2, 3 or 4-pyridyl; 2, 4 or 5-pyrimidinyl; 2 or 3-thiophenyl; 2,4, or 5-(1,3)-oxazolyl; 2,4 or 5-(1,3)-thiazolyl; 2 or 4-imidazolyl; 3 or 5-symtriazolyl.

Carboxylic acid groups can be esterified by known means, for example, treatment with an appropriate alcohol under acidic conditions or by treatment with a suitable alkyl halide. A carboxylic acid (carboxylate) can also be reduced one oxidation level to an aldehyde which in turn can be reduced one more oxidation level to an alcohol. Suitable reductive procedures are known in the art and may include treatment with hydride reagents, such as $LiAlH_4$, diisobutylaluminum hydride (DIBAL-H), or borohydrides (such as $NaBH_4$). Corresponding alcohols can be alkylated or acylated using standard procedures. Suitable alkylating agents include alkyl halides, e.g., methyl, ethyl and propyl chloride, bromide or iodide, and dialkyl sulfates such as dimethyl sulfate and diethyl sulfate. Suitable acylating agents include carboxylic acids, chlorides and anhydrides.

Carboxylic acids may be converted to amides by treatment with a suitable amine in the presence of a catalyst or coupling agent such as dicyclohexylcarbodiimide (DCC). Amides may also be prepared by treating an acid chloride with a suitable amine. In turn, an amide (or nitrile) can be reduced with a suitable reducing agent e.g., $LiAlH_4$, to an amine. Acylation or alkylation of an amine can be carried out as described above. Further methods for the interconversion of these groups are described in references such as Larock, R C, *Comprehensive Organic Transformations,* VCH Publishers, 1989, Larock, R C, *Comprehensive Organic Synthesis: A Guide to Functional Group Preparations,* John Wiley and Sons Ltd., 1989; and Smith, M B et al., *March's Advanced Organic Chemistry: Reactions, Mechanisms, and Structure,* 5th Edition, Wiley-Interscience, 2001. The contents of these 3 documents are incorporated herein by reference.

As is well-known in the art, a nitrile group is at the same oxidation level as a carboxylic acid or amide group and can be converted into these groups by known means, for example, by treatment with strong aqueous acid or base.

An alkylene chain can be lengthened, for example, by the Arndt-Eistert synthesis wherein an acid chloride is converted to a carboxylic acid with the insertion of $CH_2$. Thus, a carboxylic acid group can be converted to its acid chloride derivative, for example by treatment with $SO_2Cl_2$. The acid chloride derivative can be reacted with diazomethane to form the diazoketone which can then be treated with $Ag_2/H_2O$ or silver benzoate and triethylamine. The process can be repeated to further increase the length of the alkylene chain. Alternatively, an aldehyde (or keto) group could be subjected to Wittig-type reaction (using e.g., $Ph_3(P)=CHCO_2Me$) to produce the $\alpha,\beta$-unsaturated ester. Hydrogenation of this double bond yields the alkylene chain that has been increased in length by two carbon atoms. In a similar manner, other phosphoranes can be used to generate longer (and optionally substituted, branched or unsaturated) carbon chains.

It should be evident that chemical manipulation of a substituent at the 2-position in the sugar backbone of Formula I may require protection of other potentially reactive groups, such as the hydroxy groups, in the molecule. Suitable protective groups for use under the appropriate conditions, as well as methods for their introduction and removal are well-known in the art and are described in Greene T W et al., *Protective Groups in Organic Synthesis,* $3^{rd}$ ed, John Wiley and Son, 1999, the contents of which are incorporated herein by reference. A further aspect of this invention are these protected M6P derivatives.

Salts, Derivatives and Prodrugs

The term "salt, derivative or prodrug" includes any pharmaceutically acceptable salt, ester, solvate, hydrate or other compound which, upon administration to a subject, is capable of generating (either directly or indirectly) a compound as described herein. However, it will be appreciated that pharmaceutically "unacceptable" salts also fall within the scope of the invention since these may be used to prepare pharmaceutically acceptable salts. Suitable pharmaceutically acceptable salts include, but are not limited to, salts of pharmaceutically acceptable:

(a) inorganic acids such as hydrochloric, sulfuric, phosphoric, nitric, carbonic, boric, sulfamic, and hydrobromic, or (b) organic acids such as acetic, propionic, butyric, tartaric, maleic, hydroxymaleic, fumaric, maleic, citric, lactic, mucic, gluconic, benzoic, succinic, oxalic, phenylacetic, methanesulfonic, toluenesulfonic, benezenesulfonic, salicylic sulfanilic, aspartic, glutamic, edetic, stearic, palmitic, oleic, lauric, pantothenic, tannic, ascorbic and valeric.

Base salts include, but are not limited to, those formed with pharmaceutically acceptable cations, such as sodium, potassium, lithium, calcium, magnesium, ammonium and alkylammonium. In particular, cationic salts are within the scope of this invention, e.g., sodium or potassium salts; also included are alkyl (e.g., methyl, ethyl) phosphoesters.

Basic nitrogen-containing groups may be quaternized using: (1) a lower alkyl halide, such as methyl, ethyl, propyl or butyl chloride, bromide or iodide; (2) dialkyl sulfates, e.g., dimethyl or diethyl sulfate; and others.

The compounds of the invention may be in crystalline form either as the free compounds or as solvates (e.g., hydrates) both of which classes are within the scope of this invention. Methods of solvation are routine in the art.

Any prodrug of a compound of formula I is within the scope and spirit of the invention. The term "pro-drug" is used in its broadest sense to encompass those derivatives that are converted in vivo to the compounds of the invention. Such derivatives are readily apparent to those skilled in the art, and include, for example, compounds in which (1) a free hydroxy group is converted into an ester (such as an acetate), or (2) a free amino group is converted into an amide. Procedures for acylating the compounds of the invention are well known in the art and include reaction with an appropriate carboxylic acid, anhydride or chloride in the presence of a suitable catalyst or base.

T Lymphocytes and Their Migration

By the term "T lymphocyte" or "T cell" is intended a cell of the lymphocyte lineage which is thymus-derived in origin, as is well known in the art. See any textbook of immunology, for example, Abbas et al., supra; Janeway et al., supra; Roitt et al., supra; Klein, J, supra), which references are hereby incorporated by reference. As is known in the art, a variety of defined subsets of T cells exist in the body, such as CD4+ T helper cells, CD8+ cytotoxic T cells and the like. For the purposes of the present invention, methods of inhibiting migration of T lymphocytes are directed to multiple T cell subsets, with no established preference for T cells of any given subset.

The T lymphocytes of the present invention may be derived from an established T cell line or clone maintained in cell culture, or may be taken from the blood, lymph or organized lymphatic tissue of a cell donor. By the term "organized lymphatic tissue" is intended any tissue or organ which contains large collections of lymphocytes, including, but not limited to, thymus, bone marrow, spleen, LN, gut-associated lymphatic tissue, bronchial-associated lymphatic tissue and skin-associated lymphatic tissue. A preferred source of T cells for the present invention is the site of an ongoing antigen-specific response, such as a draining LN in a subject immunized sc, intradermally or intracutaneously, or from the circulation of such a subject.

By the term "antigen-primed" is intended a subject to which has been administered a dose of the antigen of interest prior to obtaining lymphocytes. The dose, route and timing of antigen administration will be easily determined by one of skill in the art without undue experimentation, and includes, but is not limited to, the doses, routes and time intervals disclosed herein.

By the term "activated T lymphocyte" or "activated T cell," as used herein, is intended a T cell which has been exposed to an activating agent. Preferred activating agents for the present invention include the specific antigen or a polyclonal activator such as a mitogen, capable of inducing a response by that T cell. Such responses include a large number of intermediary metabolic changes, induction of macromolecular synthesis, such as DNA, RNA or protein synthesis, cell division, and the like, as is well-known in the art. Suitable non-antigen-specific agents capable of activating T cells are known in the art and include, but are not limited to, mitogens (polyclonal T cell activators) such as concanavalin A and phytohemagglutinin. Additional activating agents are antibodies to T cell-surface structures, including but not limited to, antibodies to the CD3 cell-surface molecule, antibodies to the CD2 cell-surface molecule, antibodies to the CD28 cell-surface molecule, and the natural ligands of CD2 or CD28. Other activating agents include phorbol esters, such as phorbol myristate acetate, or a combination of a phorbol ester and a calcium ionophore, such as ionomycin. Also intended as T cell activating agents are antibodies to T cell receptor chains, specific for either the constant or the variable portions of those chains. Any activation of T lymphocytes in vitro may or may not include the addition of T cell growth factors or stimulatory factors, such as IL1, IL2 or IL4, etc., to the culture medium for part or all of the activation interval. Activation, among other effects, produces changes in T cell membrane components, modifies T cell traffic in the body, and induces expression of enzymes that may affect the way in which T cells exit from blood and transit through tissues, as is described in more detail below.

As noted in the Background section, above, T lymphocytes are known to migrate from the blood stream into tissues, including tissues in which an antigen is present for which antigen the cells are specific and to which they can respond. One way to assess T lymphocyte migration is to label T lymphocytes (or a broader population of lymphoid or blood cells that includes T lymphocytes, preferably enriched to at least 80%, more preferably at least 90% T lymphocytes). The numbers or percentages of T lymphocytes are assessed using routine methods, for example using antibodies specific for T cell markers, preferably CD3) in serologic (immunoassay), flow cytometric or other immunofluorescence-based methods, or immunochemical techniques.

The labeled cells are administered by injection or infusion, preferably intravenously (iv), into a subject, and their presence in a selected site, tissue or organ is determined by subjecting the desired tissue to an appropriate detection method in vivo or ex vivo.

Many detectable labels are well known for use herein. General classes of labels which can be used in evaluating agents that are useful for the present invention include radioactive isotopes, paramagnetic isotopes, and compounds which can be imaged by positron emission tomography (PET), fluorescent or colored compounds, etc. Suitable detectable labels include radioactive, fluorescent, fluorogenic, or chromogenic labels.

Useful radiolabels (radionuclides), which are detected by measuring radioactivity in a gamma counter, scintillation counter, by autoradiography, etc., include $^3$H, $^{14}$C, $^{35}$S, $^{51}$Cr, $^{125}$I and $^{131}$I. Other useful radionuclides are $^{99}$Tc, $^{111}$In, $^{97}$Ru, $^{67}$Cu, $^{67}$Ga, $^{68}$Ga, $^{72}$As, $^{89}$Zr, $^{90}$Y and $^{201}$Tl. If whole tissue counting is to be used, a preferred radionuclide is one that is not reutilized once it has been lost from the interior of a cell into which it was originally incorporated. That property permits a more direct relationship to be described between the amount of radioactivity (counts/min. or CPM) at a selected site or tissue, and the number of cells that have migrated to that location. $^{51}$Cr (in the form of (Na$_2$$^{51}$CrO$_4$) is particularly preferred. In another embodiment, cells may be labeled with $^{125}$I-iododeoxyuridine which is taken up by cells and may be incorporated into their DNA.

Common fluorescent labels include fluorescein, rhodamine, dansyl, phycoerythrin, phycocyanin, allophycocyanin, o-phthaldehyde and fluorescamine. The fluorophore, such as the dansyl group, must be excited by light of a particular wavelength to fluoresce. See, for example, Haugland, R P *Handbook of Fluorescent Probes and Research Chemicals*, Sixth Ed. (or later), Molecular Probes, Eugene, Oreg., 1996).

It situ detection of the detectable label may be accomplished by removing a histological specimen from a subject and examining it by microscopy under appropriate conditions to detect the label. Those of ordinary skill will readily appreciate that any of a wide variety of histological methods (such as staining procedures) can be modified in order to achieve such in situ detection.

Thus, in a preferred embodiment, T cell migration is evaluated after iv injection of labeled, preferably $^{51}$Cr-labeled, antigen-specific T cells into a mammal which has the antigen present at one or more discrete sites that can be sampled. For example, it is possible to assess the degree to which the injected T cells have accumulated in an antigen-containing tissue by measuring the amount of radioactivity present in the tissue or analyzing the tissue histologically to determine the number of infiltrating labeled cells (e.g., by autoradiography).

A migration-inhibitory agent such as a composition of the present invention, or a candidate agent, is tested for its ability to inhibit such T cell migration using any known or yet to be developed assay.

In one embodiment, animals are immunized with an antigen to stimulate antigen-specific T cells. The antigen is preferably one that is associated with an immunopathological condition, such as an autoimmune disease, and may be a self antigen (autoantigen), a foreign antigen that cross reacts with or mimics a self antigen (i.e., a case of antigenic mimicry).

In a preferred embodiment, this "immunization" is accompanied by the administration of a potent immunological adjuvant. For an extensive description of adjuvants, see, for example, *A Compendium of Vaccine Adjuvants and Excipients (2nd Edition)*, Vogel, F R et al., available from the NIAID web site (niaid.nih.gov/daids/vaccine/pdf/compendium.pdf); see also Gregoriades, G et al., *Immunological Adjuvants and Vaccines*, Plenum Press, New York, 1989; Bennett, B et al., *J. Immunol. Meth.* 153:31-40 (1992). Examples of adjuvants include Complete Freund's Adjuvant (CFA), a mineral oil adjuvant employing a water-in-oil emulsion It contains paraffin oil, killed mycobacteria and mannide monoosleate. Incomplete Freund's Adjuvant (IFA) is a mineral oil adjuvant similar to CFA but without the mycobacteria. Montanide ISA (incomplete seppic adjuvant) is a mineral oil adjuvant that uses mannide oleate as the major surfactant component. The Ribi Adjuvant System™ (RAS) is an oil-in-water emulsion that contains detoxified endotoxin and mycobacterial cell wall components in 2% squalene. Multiple formulations are commercially available. TiterMax® is a water-in-oil emulsion that combines a synthetic adjuvant and microparticulate silica with the metabolizable oil squalene. The copolymer is the immunomodulator component. Antigen is bound to the copolymer and presented to the immune cells in a highly concentrated form. Syntex Adjuvant Formulation (SAF™) is a preformed oil (squalene)-in-water emulsion that uses a block copolymer for a surfactant. A muramyl dipeptide derivative is the immunostimulatory component. Aluminum salt adjuvants are generally weaker adjuvants than emulsion adjuvants and are therefore used with more strongly immunogenic antigens. In a nitrocellulose-adsorbed antigen, the nitrocellulose is basically inert while slow degradation of nitrocellulose paper allows prolonged release of antigen. Encapsulated or entrapped antigens permit prolonged release of antigen over time. Immune-stimulating complexes (IS-COMs) are antigen modified saponin/cholesterol micelles. Stable structures are formed which rapidly migrate to draining lymph nodes. Both cell-mediated and humoral immune responses are induced. Examples are Quil A and QS-21.

At an appropriate time after immunization, for example 7-14 days, T cells are harvested from the animal. Any lymphatic organ or tissue, or a body fluid rich in lymphocytes such as blood or lymph, may be the source of these T cells. Preferred sources are the spleen or, more preferably, draining LNs that drain the immunization site. Lymphocytes are harvested from these sources, and T cells may be further isolated or enriched from these lymphocyte populations using conventional T cell enrichment methods.

These T cells (or T cell enriched lymphocyte populations) are then detectably labeled (using a label described above or any other appropriate detectable label known in the art. The labeled cells are then introduced into a naïve recipient animal. Preferably, inbred mice or rats are used and the recipient and donor are syngeneic or at least matched at the MHC so that the infused cells are histocompatible with the recipient. The labeled T cells are preferably injected or infused systemically, preferably iv or ip, that they may circulate and migrate into a target tissue. The target tissue is one that either naturally expresses the antigen, e.g., a self antigen, against which these T cells are specific. Alternatively, a foreign antigen may be provided to the recipient animals via local or regional administration. In either case, a proportion of the infused or injected labeled T cells will migrate to and accumulate in the site or tissue or organ in which the antigen is present and expressed in a form recognizable by the T cells.

For example, in the case of diseases of the central nervous system (CNS) involving a CNS antigen, or their animal models, such as MS and EAE, myelin basic protein (MBP) is a disease-associated antigen. In MS or EAE, T cells localize in the brain and spinal cord, often as extravasated collections of cells in the form of perivascular cuffs.

To test inhibitors of T cell migration in the setting of these CNS diseases, it is desirable to have a stable reproducible measure of T lymphocyte movement into and through brains. The number or proportion of labeled cells at a selected site can be determined by the appropriate detection method, as discussed above. This can also be done in a visual form, e.g., by histochemical or other histological methods.

As noted above, when testing a migration inhibitory agent in a system based upon a foreign antigen, a depot or site of antigen accumulation is created as part of the test. Preferred routes of administering the antigen is s.c., intradermal or topical (as with a reactive hapten such as picryl chloride, picryl sulfonic acid, or fluorodinitrobenzene, or dinitrobenzene sulfonic acid. A certain number of T cells will migrate to the site of antigen or to a draining LN if sufficient time has elapsed for some of the antigen to reach the draining LN.

One approach, exemplified herein, is induction of a cell-mediated immune reaction of the type that was once classified as a "type IV hypersensitivity" reaction.

The foregoing methods are recognized and well understood by those skilled in the art and the underlying principles can be found in any immunology textbook such as those cited above. Here donor animals are sensitized to a self protein (in practice, skin is the easiest tissue to use) by chemically modifying the protein(s) in this tissue thereby allowing the chemical moiety to be 'seen' as 'foreign' tissue by the immune system. This is done by reacting the skin ("painting") with a 'hapten' which is usually an alkylating or arylating agent that reacts covalently with and thereby modifies protein(s) in the skin. Seven to ten days following sensitization, spleens or draining LNs are taken from the donor animals. T lymphocytes are isolated, radio- or fluorescently-labeled and transferred into naïve recipient animals by intravenous injection. Prior to cell transfer the recipient animals have had a portion of skin, for simplicity's sake usually the ear pinna, painted with the same reactive hapten. Within a short time of cell transfer sensitized T cells begin to accumulate in the hapten-modified tissue, 8-24 hours later the tissue can be removed and the cell accumulation assessed. In the case of fluorescently-labeled cells, their accumulation is assessed histologically or histochemically, and in the case of radiolabeled cells, accumulation is assessed by counting radioactive decay in a suitable device. Typically, the agents of the present invention can inhibit T cell accumulation in this model by between about 20% and 85%. In this model, it preferred to utilize a relatively pure or enriched T lymphocyte population because the inhibitory compositions of the present invention are not expected to interfere with B lymphocyte migration.

Vascular endothelial cells (VECs) grown in culture will attain confluence and deposit an endothelial subcellular matrix. The cells and matrix are akin to the same components found in blood vessels in vivo (Jaffe, E A et al., *J. Clin. Invest.* 52:2745-2756 (1973)). Activated T cells migrate through this matrix in the same fashion as they do through tissues in the body. This migration can be studied and put into practice by growing VECs on special devices that contain a fenestrated barrier between two chambers through which cells can move. When VEC are cultured in the upper chamber of such a device, they will grow to confluence and deposit a subcellular matrix over the fenestrated barrier. If activated T cells are suspended above the VEC layer in this chamber, they will migrate through it and degrade the subcellular matrix, and migrate further through the fenestrations into the lower chamber where they can be observed, counted, etc. The efficacy of agents that can inhibit the ability of T cells to migrate through this matrix can thus be determined by placing the agent in either or both chambers during the culture period when the T cells are present. Efficacy of the agent is quantified by comparing the number of T cells in the lower chambers (i.e., migrated cells) of the agent-treated group versus the number of T cells in the lower chamber of the control device (no agent or a negative control agent). This method is commonly used to study cell migration through vascular endothelium and is well known in the art. See, for example, Poggi, A et al. *Europ. J. Immunol.* 27:2345-2350 (1997); Hauzenberger, E et al., *Transplantation.* 69:1837-1849. (2000); Borthwick, N J et al., *Immunology* 90:272-280 (1997); Mohle, R et al., (1997) *Blood.* 89:72-80 (1997); and Lou, J et al., *Lab. Invest.* 79:1015-1025. (1999), each of which is incorporated by reference.

Compounds of the present invention that inhibit T lymphocyte emigration from within the blood vessels into surrounding tissues are useful in the treatment of cell-mediated inflammatory diseases and conditions. The ability of these compounds to act in this way may be determined by the tests described in the Examples included hereinafter. Nonlimiting examples of such inflammatory diseases or conditions which may be treated by the compounds of the present invention include RA, MS, ADE, psoriasis, Crohn's disease, T cell-mediated dermatitis, stromal keratitis, uveitis, thyroiditis, sialitis and type I diabetes.

As used herein, the term "inhibit" includes its general meaning, i.e., stopping, preventing, restraining, minimizing or slowing, T lymphocyte migration from the blood into an extra vascular site, such as surrounding tissues. The term "inhibit" is also intended to mean reversing the progression or severity of symptoms of a disease or disorder.

Compounds that inhibit T cell migration are therefore be useful in "treating" cell-mediated immune or inflammatory diseases and conditions. The term "treating" (and is intended to include "prevention," "protection from," "suppression of" or "therapy of" of a disease or disorder. "Prevention" generally involves administration of the present compound or pharmaceutical composition prior to the induction or appearance of the disease. Thus, for example, in the animal model, EAE, successful administration of a the therapeutic composition prior to injection of the encephalitogen (e.g., MBP) that induces the disease results in "prevention" of the disease. "Suppression" generally involves administration of the compound after the inductive event but prior to the clinical appearance of the disease. Again, using the EAE example, successful administration of a protective composition after injection of the encephalitogen, but prior to the appearance of neurological symptoms, comprises "suppression" of the disease. "Therapy" generally involves administration of the compound after the appearance of the disease. In the EAE example, successful administration of a composition after injection of the encephalitogen and after clinical signs have developed comprises "therapy" of the disease. It will be understood that in human medicine, it is not always possible to distinguish between "preventing" and "suppressing" since the ultimate inductive event or events may be unknown, latent, or the patient is not ascertained until well after the occurrence of the event or events. Therefore, it is common to use the term "prophylaxis" as distinct from "treatment" to encompass both "preventing" and "suppressing" as defined herein. The term "treatment" as used herein is meant to include "prophylaxis." As such, the present methods include both therapeutic and/or prophylactic administration of the compounds of the invention to "treat" a disease or condition.

The compounds of the invention may be used to treat humans or other mammalian subjects. The compounds of the invention are considered to be particularly suitable for the treatment of human subjects. Non-human subjects may include primates, livestock animals (e.g., sheep, cows, horses, goats, pigs) domestic companion animals (e.g., cats, dogs) laboratory test animals (e.g., mice, rats, guinea pigs, rabbits) or captive wild animals.

The compounds of the invention are administered to the subject in a treatment-effective or prophylaxis-effective amount. As used herein, such an "effective amount" is intended to include an amount that at least partially attains the desired effect, or delays the onset of, or inhibits the progression of, or halts or reverses altogether the onset or progression of the particular disease or condition being treated.

As used herein, the term "effective amount" or "effective dose" relates to an amount or dose of compound (or pharmaceutical composition thereof) which, when administered according to a desired dosing regimen, provides the desired therapeutic effect. Dosing may occur at intervals of minutes, hours, days, weeks, months or years or continuously over any one of these periods. Suitable dosages lie within the range of about 0.1 ng per kg of body weight to 1 g per kg of body weight per dosage. The dosage is preferably in the range of 1 μg to 1 g per kg of body weight per dosage, such as is in the range of 1 mg to 1 g per kg of body weight per dosage Suitably, the dosage is in the range of 1 μg to 500 μg per kg of body weight per dosage, such as 1 μg to 200 mg per kg of body weight per dosage, or 1 μg to 100 mg per kg of body weight per dosage. Other suitable dosages may be in the range of 1 mg to 250 mg per kg of body weight, including 1 mg to 10, 20, 50 or 100 mg per kg of body weight per dosage or 10 μg to 100 mg per kg of body weight per dosage.

Suitable dosage amounts and dosing regimens can be determined by a treating health care specialist and may depend on the particular condition being treated, the severity of the condition, as well as the general health, age and weight of the subject.

The active ingredient may be administered in a single dose or a series of doses. While it is possible for the active ingredient to be administered alone, it is preferable to present it to a subject as a composition, preferably as a pharmaceutical composition. The formulation of such compositions are well know to those skilled in the field. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include supplementary anti-inflammatory or other physiologically active agents where appropriate.

The carrier, diluent or excipient must be pharmaceutically "acceptable" in the sense of being compatible with the other ingredients of the composition and not injurious to the subject. Compositions include those suitable for oral, rectal, nasal, topical (including buccal and sublingual), vaginal or parenteral (including sc, intramuscular (im), intravenous (iv) and intradermal (id)) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

The administration of the present compounds and pharmaceutical compositions may employ any route and any means that achieves the necessary distribution of the compound to achieve its desired inhibitory effect. Systemic routes are preferred, either oral, parenteral or both. Local or regional administration, such as intra-articular and topical, is also contemplated. For example, administration may be by injection or infusion. Preferred routes include intravenous, intramuscular, subcutaneous, intranasal, intrapulmonary, intraperitoneal, intrathecal, and intradermal. Rectal administration, e.g., by suppository is also included. Additionally or alternatively, administration may be transdermal (using a patch or other similar device), by osmotic minipump, or by any other controlled release method or formulation, all of which are well-known in the art (see for example European Patent publications EP 92918, EP 0166596; U.S. Pat. Nos. 4,789,516, 4,806,621, 4,877,606, 4,906,474, 4,925,677, 4,942,035; Hsieh, DST et al., *J. Pharm. Sci.* 72: 17-22 (1983); Kaitsu, I et al., *J. Controlled Release* 6: 249-263 (1987); Goedemoed, J H et al., *Makromol. Chem. Macromol. Symp.* 19: 341-365 (1988); Yang, M B. et al., *Canc. Res.* 49:5103-5107 (1989); Greig, N. et al., *J. Controlled Release* 11:61-78 (1990); Jeyanthi, R et al., *J. Controlled Release* 13:91-98 (1990); Saltzman, W M et al., *Polymer Preprints* 31-1: 2456 (1990). The dosage administered will be dependent upon the age, health, and weight of the recipient, kind of concurrent treatment, if any, frequency of treatment, and the nature of the effect desired.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid;

or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., inert diluent, preservative disintegrant (e.g., sodium starch glycolate, cross-linked polyvinyl pyrrolidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavored base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier. Compositions for topical administration, for example, dermally, may be in the form of lotions, creams, pastes, gels, ointments and the like Compositions for rectal administration may be presented as a suppository with a suitable base comprising, for example, cocoa butter, glycerin, gelatin or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients, the compounds of this invention, described above, the present pharmaceutical compositions of this invention may include other agents conventional in the art for use in the type of composition in question, for example, those suitable for oral administration may include such further agents as binders, sweeteners, thickeners, flavoring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavoring agents include peppermint oil, oil of wintergreen, cherry, orange or raspberry flavoring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulfite. Suitable lubricants include magnesium stearate, stearic acid, sodium oleate, sodium chloride or talc. Suitable time delay agents include glyceryl monostearate or glyceryl di-stearate.

The compounds of the invention may also be presented for use in veterinary compositions. These may be prepared by any suitable means known in the art. Examples of such compositions include those adapted for: (a) parenteral administration, e.g., sc, im, or iv injection as a sterile solution or suspension; (b) oral administration, external application (e.g., drenches including aqueous and non-aqueous solutions or suspensions), tablets, boluses, powders, granules, pellets for admixture with feedstuffs, pastes for application to the tongue; (c) topical application e.g., creams, ointments, gels, lotions, etc.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Having now generally described the invention, the same will be more readily understood through reference to the following examples which are provided by way of illustration, and are not intended to be limiting of the present invention, unless specified.

In the following examples temperatures were measured in degrees Celsius (° C.) and thin layer chromatograms (tlc) were determined on silica gel plates and unless otherwise specified chemical reagents were purchased from Aldrich.

EXAMPLE 1

Preparation of Chemical Compositions

Preparation of 1-(2,4-dimethyl phenyl)-6-phosphono-mannoside (Formula I; R=2,4-dimethylbenzene, n=0)

Preparation of 1-methyl-2,3,4,6-tetrabenzyl-mannoside

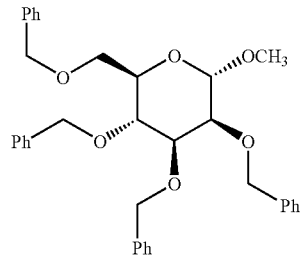

To a stirred solution of 1-methyl mannoside (64.3 g, 270 mmol) in DMF (1200 ml) was slowly added sodium hydride (~6 eq., 58 g) and stirred for ~1 hr. Tetrabutyl ammonium iodide (~0.1 eq., 10.6 g) was then added followed by benzyl chloride (12 eq., 373 g, 410 ml) and the mixture stirred overnight at room temperature. The reaction mixture was then poured into concentrated ammonia (600 ml) and stirred for 6 hr after which it was extracted with diethyl ether/light petroleum (1:1, 2×1000 ml). The combined organic layers were washed successively with water (4×1000 ml), hydrochloric acid (1000 ml) and water (2×1000 ml). The organic layer was dried (Na$_2$SO$_4$), filtered and the solvent removed (rotary evaporator). The residue was taken up in light petroleum (800 ml), ~120 g of silica gel was added and this poured onto a column of silica gel (250 g) under vacuum. The column was then eluted successively with 100% light petroleum (1600 ml, f1[800 ml], f2[800 ml]), 5% ethyl acetate/light petroleum (800 ml, f3[800 ml]), 10% ethyl acetate/light petroleum (800 ml, f4), 25% ethyl acetate/light petroleum (800 ml, f5) 50% ethyl acetate/light petroleum (800 ml, f6) and 10% methanol/dichloromethane (800 ml, f7). The title product was found in f4-7 (130.09 g, 71%). MS: [M+H]$^+$ (calc.)=555.67, [M+H]$^+$ (exper.)=555.67

Preparation of 1,6-diacetyl-2,3,4,tribenzyl-mannoside

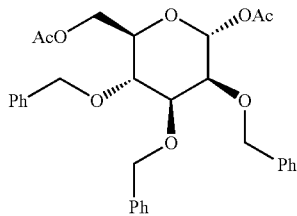

To a stirred solution of 1-methyl-2,3,4,6-tetrabenzyl-mannoside (85.37 g, 0.154 mol) in acetic acid (500 ml) and acetic anhydride (100 ml) at 0° C. under nitrogen was added concentrated sulfuric acid (2.5 ml). The reaction mixture was allowed to slowly warm to room temperature and left overnight. The reaction mixture was poured onto water (1000 ml) and extracted with diethyl ether (3×500 ml). The combined organic layers were washed successively with water (4×600 ml), sodium bicarbonate solution (2×500 ml, 400 ml of a saturated solution diluted to 1000 ml), water (1000 ml), brine (500 ml), dried (Na$_2$SO$_4$), filtered and the solvent removed. The residue was taken up in light petroleum (400 ml), ~50 g of silica gel was added and this poured onto a column of silica gel (150 g) under vacuum. The column was then eluted with 100% light petroleum (800 ml, f1), 5% ethyl acetate/light petroleum (800 ml, f2), 10% ethyl acetate/light petroleum (800 ml, f3), 25% ethyl acetate/light petroleum (800 ml, f4), 50% ethyl acetate/light petroleum (800 ml, f5), 100% ethyl acetate (800 ml, f6) and 10% methanol/dichloromethane (800 ml, f7). The title product was found in f4-6 (71.32 g, 87%). [M+H]$^+$ (calc.)=534.59, [M+H]$^+$ (exper.)=534.59

Preparation of 1-trimethylsilyl-2,4-dimethyl phenol

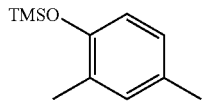

To a stirred solution of 2,4-dimethyl phenol (5.47 g, 44.8 mmol) in dry dichloromethane (120 ml) at 0° C. under nitrogen was added triethylamine (1.1 eq., 4.99 g, 6.9 ml) followed by the slow addition of trimethyl silyl chloride (1.05 eq., 5.11 g, 6.00 ml). The reaction was monitored by thin layer chromatography (10% ethyl acetate in 60-80 light petroleum) and upon completion (~2 hr) water (50 ml) was added. The organic layer was washed with water (2×50 ml), dried (Na$_2$SO$_4$), filtered and the solvent removed to give the title compound (8.13 g, 93%).

Preparation of 1-(2,4-dimethylphenyl)-6-acetyl-2,3,4,tribenzyl-mannoside

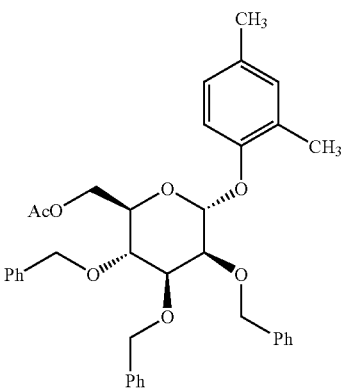

To a stirred solution of 1,6-diacetyl-2,3,4-tribenzyl-mannoside (4.74 g, 8.88 mmol) in dry dichloromethane (50 ml) at 22° C. under nitrogen was added 1-trimethylsilyl-2,4-dimethyl phenol (1.6 eq, 2.78 g, 14.3 mmol) in dry dichloromethane (25 ml) followed by the slow addition of trimethylsilyl triflouromethane sulfonate (0.4 eq., 788 mg, 0.64 ml). The reaction was monitored by thin layer chromatography (25% ethyl acetate in 60-80 light petroleum) and upon completion (~2 hr) saturated sodium bicarbonate solution (100 ml) was added. The aqueous layer was extracted with dichloromethane (100 ml). The combined organic layers were washed successively with sodium hydroxide (5×100 ml), water (2×100 ml), brine (100 ml), dried (Na$_2$SO$_4$), filtered and the solvent removed. The residue was taken up in light petroleum (100 ml), 20 g of silica gel was added and this poured onto a column of silica gel (50 g) under vacuum. The column was then eluted successively with 100% light petroleum (400 ml, f1), 5% ethyl acetate/light petroleum (800 ml, f2[400 ml], f3[400 ml]), 10% ethyl acetate/light petroleum (800 ml, f4), 25% ethyl acetate/light petroleum (400 ml, f5) 50% ethyl acetate/light petroleum (400 ml, f6) and 10% methanol/dichloromethane (400 ml, f7). The title product was found in f3 (4.35 g, 82%): [M+H]$^+$ (calc.)=596.70, [M+H]$^+$ (exper.)=596.70.

Preparation of 1-(2,4-dimethylphenyl)-6-hydroxy-2,3,4-tribenzyl-mannoside

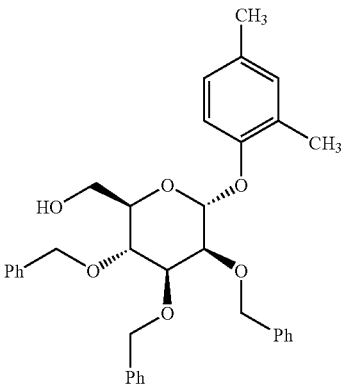

To a stirred solution of 1-(2,4-dimethylphenyl)-6-acetyl-2,3,4-tribenzyl-mannoside (34.4 g, 57.7 mmol) in dry methanol (250 ml) at 22° C. with a soda lime tube in place was added sodium methoxide (5.33 g) until a slight color change occurred. The reaction was monitored by thin layer chromatography (25% ethyl acetate in 60-80 light petroleum) and upon completion (~1 hr) the solvent was removed. The residue was shaken with water/dichloromethane (1:1, 500 ml). The organic layer was removed and the aqueous layer was extracted with dichloromethane (250 ml). The combined organic layers were washed with water (250 ml), dried (Na$_2$SO$_4$), filtered and the solvent removed. The residue was taken up in light petroleum (200 ml), 50 g of silica gel was added and this poured onto a column of silica gel (100 g) under vacuum. The column was then eluted successively with 100% light petroleum (800 ml, f1), 5% ethyl acetate/light petroleum (800 ml, f2), 10% ethyl acetate/light petroleum (800 ml, f3), 25% ethyl acetate/light petroleum (800 ml, f4) and 10% methanol/dichloromethane (800 ml, f5). The title product was found in f3,4 (22.63 g, 82%): [M+H]$^+$ (calc.) =554.67, [M+H]$^+$ (exper.)=554.67.

Preparation of 1-(2,4-dimethylphenyl)-6-formyl-2,3, 4-tribenzyl-mannoside

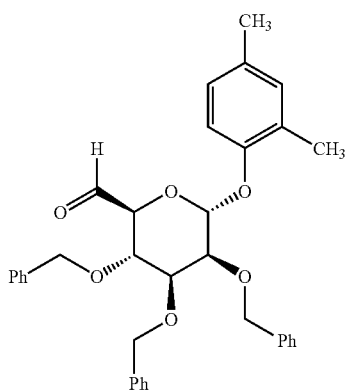

To a stirred solution of dimethyl sulfoxide (4 eq., 11.4 g, 10.3 ml) in dry dichloromethane (300 ml) at −60° C. under nitrogen was slowly added a solution of oxalyl chloride (1.5 eq., 9.26 g, 6.3 ml) in dry dichloromethane (50 ml). After 5 min a solution of 1-(2,4-dimethylphenyl)-6-hydroxy-2,3,4-tribenzyl-mannoside (20.2 g, 36.4 mmol) in dry dichloromethane (120 ml) was slowly added. The reaction mixture was stirred for a further 1 hr at −60 C after which triethylamine (8 eq, 29.4 g, 40.3 ml) was added. The reaction mixture allowed to warm to room temperature, stirred for a further 1 hr and then poured onto water (500 ml). The aqueous layer was extracted with dichloromethane (2×500 ml). The combined organic layers were washed with water (3×500 ml), dried (Na$_2$SO$_4$), filtered and the solvent removed to give crude title compound. The residue was taken up in light petroleum (200 ml), 30 g of silica gel was added and this poured onto a column of silica gel (150 g) under vacuum. The column was then eluted with 100% light petroleum (800 ml, f1), 5% ethyl acetate/light petroleum (800 ml, f2), 10% ethyl acetate/light petroleum (800 ml, f3), 25% ethyl acetate/light petroleum (800 ml, f4), 50% ethyl acetate/light petroleum (800 ml, f5) and 10% methanol/dichloromethane (800 ml, f6). The title product was found in f3,4 (19.16 g, 95%): [M+H]$^+$ (calc.)=552.65, [M+H]$^+$ (exper.)=552.65.

Preparation of 1-(2,4-dimethylphenyl)-6-diisopropyl phosphono-2,3,4-tribenzyl-mannoside

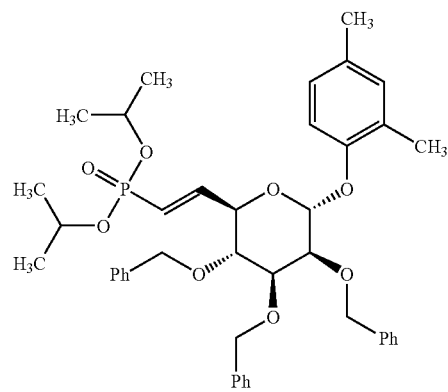

To a stirred suspension of sodium hydride (60%, 1.1 eq, 1.57 g) in dry tetrahydrofuran (100 ml) at 0° C. under nitrogen was added tetraisopropyl methylene diphosphonate (1.2 eq, 14.3 g, 13.3 ml). After 10 min a solution of 1-(2,4-dimethylphenyl)-6-aldehydo-2,3,4-tribenzyl-mannoside (19.16 g, 34.7 mmol) in dry tetrahydrofuran (100 ml) was slowly added. The reaction mixture was allowed to warm to room temperature and after 2.5 hr poured into a saturated ammonium chloride solution (200 ml). The reaction mixture was extracted with dichloromethane (1×400 and 1×200 ml). The combined organic layers were washed with water (2×200 ml), dried (Na$_2$SO$_4$), filtered and the solvent removed. The residue was taken up in light petroleum (300 ml), 50 g of silica gel was added and this poured onto a column of silica gel (150 g) under vacuum. The column was then eluted successively with 100% light petroleum (800 ml, f1), 10% ethyl acetate/light petroleum (800 ml, f2), 25% ethyl acetate/light petroleum (800 ml, f3), 50% ethyl acetate/light petroleum (800 ml, f4) and 10% methanol/dichloromethane (800 ml, f5). The title product was found in f3,4 (22.54 g, 90%): [M+H]$^+$ (calc.) =714.82, [M+H]$^+$ (exper.)=714.82.

Preparation of 1-(2,4-dimethylphenyl)-6-diisopropyl phosphono-mannoside

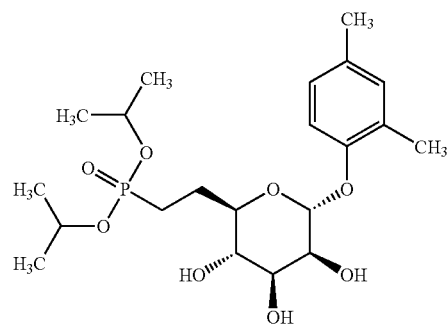

A solution of 1-(2,4-dimethylphenyl)-6-diisopropyl phosphono-2,3,4-tribenzyl-mannoside (7.11 g, 10.0 mml) and palladium on charcoal (10%, 5.18 g) in a ethanol, water acetic acid mix (95:5:1, 100 ml) was shaken under a hydrogen atmosphere (~60-65 psi) in a Parr apparatus and monitored by thin layer chromatography (Ethyl acetate/ethanol/water, 85:10:5) and mass spectroscopy. Upon completion (several days) the reaction mixture was filtered and the solvent removed. The residue was taken up in dichloromethane (100 ml), 50 g of silica gel was added and this poured onto a column of silica gel (100 g) under vacuum. The column was then eluted with 100% dichloromethane (400 ml, f1), 2.5% methanol/dichloromethane (800 ml, f2), 5% methanol/ dichloromethane (800 ml, f3), 10% methanol/dichloromethane (800 ml, f4), 25% methanoldichloromethane (400 ml, f5) and 100% methanol (400 ml, f6). The title product was found in f3,4,5 (4.10 g, 92%): $[M+H]^+$ (calc.)=446.47, $[M+H]^+$ (exper.)=446.47.

Preparation of
1-(2,4-dimethylphenyl)-6-phosphono-mannoside

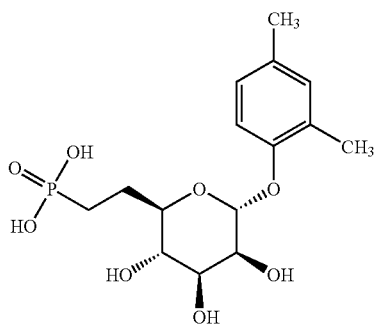

To a stirred solution of 1-(2,4-dimethylphenyl)-6-diisopropyl phosphono-mannoside (5.74 g, 12.9 mmol) in dry acetonitrile (200 ml) at room temperature under nitrogen was added triethylamine (10 eq, 13.0 g, 17.8 ml), followed by sodium iodide (10 eq, 19.3 g) and the slow addition of chlorotrimethyl silane (10 eq, 14.0 g, 16.3 ml). The reaction was stirred overnight then filtered through a plug of celite which was washed with 2% triethylamine in dichloromethane (200 ml). The solvent was removed, the residue was taken up in 2% triethylamine in dichloromethane (400 ml) and washed with water (2×200 ml). The organic layer was dried ($Na_2SO_4$), filtered and the solvent removed. The residue was taken up in dichloromethane/water (1:1, 400 ml), trifluoroacetic acid added (5 ml) and the stirred mixture warmed to 55° C. for 1 hr and the dichloromethane allowed to evaporate off. The solution was allowed to cool, wash with dichloromethane and the solvent removed to give impure title compound. The was then purified on reverse phase silica to give pure title compound (3.41 g, 77%): $[M+H]^+$ (calc.)=362.31, $[M+H]^+$ (exper.)= 362.31.

In a similar manner to the foregoing procedure and using the appropriate reagents, the following compounds were prepared. Compound (d) was tested and found to be pharmaceutically effective as defined herein; compounds (a)-(c) are also be shown to be pharmaceutically effective.

(a) 1-(2,4,6-trimethylphenyl)-6-phosphono-manoside, $[M+H]^+$ (calc.)=376.34, $[M+H]^+$ (exper.)=376.34.
(b) 1-(2-methyl,4-chlorophenyl)-6-phosphono-mannoside, $[M+H]^+$ (calc.)=382.73, $[M+H]^+$ (exper.)=382.73.
(c) 1-(2-methyl,4-fluorophenyl)-6-phosphonomannoside, $[M+H]^+$ (calc.)=366.27, $[M+H]^+$ (exper.)=366.27.
(d) 1-(2-methyl,4-trifluoromethyl)-6-phosphonomannoside, $[M+H]^+$ (calc.)=416.28, $[M+H]^+$ (exper.)=416.28.

EXAMPLE 2

Inhibition of T-lymphocyte Migration Across Rat Brain Endothelial Cell Layer

Preparation of Brain Endothelial Cells (ECs)

Vascular ECs were isolated from rat brain capillaries of 6 to 8 week old Lewis rats according to the method of Risau, W et al., 1990, *J. Cell Biol.* 110:1757-1766 (which is incorporated herein by reference). Colonies of ECs were purified from astroglial cells and pericytes using anti-Thy1.1-antibody and complement-mediated lysis to remove unwanted Thy1.1+ cells.

The EC colonies were grown, using conventional methods, in Dulbecco's Modified Eagle's Medium (DMEM)-high glucose, supplemented, with 20% fetal calf serum (FCS), glutamine, pyruvate, nonessential amino acids, HEPES buffer and antibiotics (kanamycin, amphotericin), and heparin (all from GIBCO). Cultures were supplemented with 150 μg/ml "endothelial growth supplement" from Collaborative Biomedical Products. Upon reaching confluence, EC cultures were washed with 0.2% EDTA in phosphate buffered saline (PBS), trypsinized (Trypsin-EDTA, 0.1% final concentration), washed and re-treated with anti-Thy1.1 antibody for 40 min, washed and incubated with complement sufficient to lyse all Thy1.1+ cells (Behringwerke, AG, Marburg, Germany) at room temperature.

ECs were then plated on Matrigel®-coated 6.5 mm Transwells, 5 mm pore size (Corning Costar Corporation, Cambridge, Mass.). Presence of ECs and confluence of the monolayer were checked by measuring the electrical resistance (World Precision Instruments, New Haven, U.S.A., model EVOM-G) and by staining with FITC-labeled phalloidin (Sigma).

Myelin Basic Protein (MBP)-Specific T Cell Lines

To study the effect of agents of the present invention on T lymphocyte migration, MBP-specific T lymphocyte cell lines were generated according to the method of Ben-Nun et al., *Europ. J. Immunol.* 11:195-199 (1981); incorporated herein by reference) starting with lymphocytes from the LNs of Lewis rats that had been immunized with MBP in complete Freund's adjuvant (CFA). These cells were used for migration studies during the first 4 days of their propagation in IL-2-containing medium, following MBP restimulation in the presence of antigen-presenting cells (irradiated spleen or thymus cells from normal Lewis rats).

These stimulated T lymphocytes were radiolabeled with $^{51}Cr$ ($Na^{51}CrO_4$, 37 MBq/ml, Amersham, UK) for 30 minutes at 37° C. with occasional agitation, they were then washed three times with DMEM and placed into the upper chamber of the Transwells at 5×10$^5$ cells in 100 μl of "migration medium." Test and control substance were included in the upper wells at final concentrations of 0.1, 1 and 10 mM. Cell migration was assessed visually by light microscopy to gauge progress of the experiment. The experiment was terminated after 6 hours, whereupon the undersurface of the membrane filters were rinsed twice with 100 μl of ice-cold PBS-0.2% EDTA and combined with the medium of the lower chamber of the well. The combined material was counted for radioactivity in a gamma counter (Packard Auto-Gamma 5650 (Downer's Grove Ill., USA) gamma counter. Each "treatment" group was run in triplicate (test agent, control agent (glucose 6-phosphate) and no treatment).

The results from a typical experiment are shown in Table 1, below. The value for the glucose 6-phosphate was not statistically different from no treatment. Inhibition values are in comparison with the negative control.

TABLE 1

| Test substance (10 mM) | % inhibition (±SEM) |
| --- | --- |
| 1-(2,4-dimethylphenyl)-6-phosphono-mannoside. | 90 ± 4 |
| 1-(2,4,6-trimethylphenyl)-6-phosphono-mannoside. | 80 ± 4 |
| 1-(2-methyl,4-chlorophenyl)-6-phosphono-mannoside. | 65 ± 4 |
| 1-(2-methyl,4-fluorphenyl)-6-phosphono-mannoside | 53 ± 2 |
| 1-(2-methyl,4-trifluoromethyl)-6-phosphono-mannoside | 88 ± 3 |
| negative control - glucose-6-phosphate | 0 ± 5 |

The results show that the five different M6P derivatives (phosphono-mannosides) significantly inhibited T cell migration across a monolayer of brain-derived ECs in vitro.

EXAMPLE 3

Inhibition of Lymphocyte Migration into Lymphoid Tissue

Lymphocytes were obtained from spleens of 6-8 week old female specific pathogen-free Balb/c mice (19-21 g). Single cell suspensions prepared by conventional means (pushing through a stainless steel screen). Red blood cells were lysed by treating with a solution of bicarbonate buffered ammonium chloride-EDTA (pH 7.3) and the preparation strained through a Falcon 2350 cell strainer. All cell preparative steps were performed on ice. Cell were suspended in a conventional lymphocyte culture medium (DMEM plus glucose, folic acid, L-asparagine, sodium bicarbonate, L-glutamine, sodium pyruvate, HEPES, 2-mercaptoethanol, penicillin, streptomycin, neomycin, and 2% FCS).

B lymphocytes were depleted by suspending the cells in purified rat anti-mouse CD45/B220 antibody (RA3-6B2 clone; PharMingen, USA) at a concentration of $4 \times 10^7$ cells/ml and incubated on ice for 20 minutes. An equal volume of culture medium (as above) was added and the cells centrifuged (200×g) and resuspended at a concentration of $10^7$ cells/ml in BioMag goat ant-rat IgG (H&L) ("GARIG") conjugated to magnetic beads (Bio Mag; Perseptive Diagnostics, Polysciences, Inc., USA). Following a 20 minute incubation on ice, with agitation every 5 minutes, cells binding to the GARIG/anti-CD45/B220 antibody complex were removed using magnetic separation (Dynal MPC-6, Dynal, USA). This procedure was repeated 4 times, resulting in a cell population containing approximately 80-90% T lymphocytes (determined by FACS analysis).

The cells were then washed in Hanks balanced salt solution (HBSS), resuspended in 5 ml of HBSS, and radiolabeled with $^{51}$Cr for 30 minutes at 37° C. (as described above). The labeled cells were washed in PBS, centrifuged (200×g), and a portion were resuspended at a concentration of $3 \times 10^7$ cells/ml in either PBS (negative control) or PBS containing phenyl mannoside 6-phosphate (25 mg/ml in PBS; positive control) or PBS containing the test compound (25 mg/ml), and stored on ice. Cell viability was confirmed throughout the procedures by trypan blue exclusion. Balb/c mice were injected intravenously (iv) into the lateral tail vein with 0.2 ml containing $6 \times 10^6$ labeled lymphocytes and 0.2 ml of either PBS (negative control), 5 mg positive control or 5 mg test compound. All groups of mice were weight matched (±0.5 g).

Spleens from recipient mice were removed 1.5 hours after injection, and the cell-associated radioactivity was determined using a gamma counter (as above). Results of inhibition of lymphocyte migration into the spleen were expressed as a percentage reduction in the CPM of the spleens from treated animals compared with negative controls.

The positive control compound caused 70.5% inhibition of lymphocyte migration (n=4). The phosphono-mannoside compounds of the present invention and their relative inhibition of lymphocyte migration in vivo (compared to negative controls) are presented in Table 2.

TABLE 2

Inhibition of lymphocyte migration into spleens.

| Compound | % Inhibition |
| --- | --- |
| 1-(2,4,-dimethyl phenyl)-6-phosphono-mannoside | 82.4 |
| 1-(2,4,6-trimethyl phenyl)-6-phosphono-mannoside | 85.5 |
| 1-(2-methyl,4-chlorophenyl)-6-phosphono-mannoside | 45.0 |
| 1-(2-methyl,4-fluorphenyl)-6-phosphono-mannoside | 68.0 |
| 1-(2-methyl,4-trifluoromethyl)-6-phosphono-mannoside | 87.3 |

EXAMPLE 4

Inhibition of T Lymphocyte Migration into Extralymphatic Tissues In Vivo

Spleen cell suspensions were prepared as in Example 3. Spleen donors were specific pathogen-free 6-8 week old female Balb/c mice (19-21 g) which had been sensitized one week earlier with picryl chloride (in 1% in ethanol) applied topically to a 1 cm² shaved area of abdominal skin.

B lymphocytes were depleted as described in Example 3. The enriched lymphocyte population contained approximately 85-90% T lymphocytes and <1% B cells (determined by FACS analysis).

The cells were labeled with $^{51}$Cr as in Example 3. Recipient Balb/c mice were injected iv with the labeled cells and with test or control compounds as in Example 3. In this study, however, one hour prior to this injection, the right ear of each mouse was painted with picryl chloride (0.1% in ethanol) to induce a localized antigen-specific immune response. As is known in the art, the interval between antigen-treatment and administration of test agents and migrating cells can be varied, including extensions of greater than one hour.

Between 9 and 10 hours after infusion of the radiolabeled T cells (though this can be varied), the recipient mice were euthanized by $CO_2$, their right and left ear pinnae were excised and placed in vials for gamma counting, as described above.

Results (inhibition of lymphocyte migration into the right ear pinna) were expressed as a percentage reduction in the CPM of the right ear pinnae from treated animals compared with the right ear pinnae of the negative controls. To control for non-specific migration of cells, the (CPM) radioactivity in a left (nonchallenged) ear pinna was subtracted from the CPM in the right ear pinna of the same animal prior to determining the mean for each group.

Results from a typical experiment are shown below.

TABLE 3

| Test substance (5 mg/mouse) | Route | Inhibition* |
| --- | --- | --- |
| 1-(2,4,-dimethyl phenyl)-6-phosphono-mannoside. | IV | 56.1 |

*Percent inhibition of T cell migration

EXAMPLE 5

Inhibition of Cell-Mediated Immune Disease of the Central Nervous System

Experimental autoimmune encephalomyelitis (EAE) is an inflammatory disease of the central nervous system that bears similarities to multiple sclerosis (MS) and has therefore been used extensively as an animal model of MS. Many references to this model are available in the medical and scientific literature. See, for example, Paterson, P Y, In *Textbook of Immunopathology* (Miescher, P A et al., eds) Grune & Stratton, New York, 1976, especially pp. 179-213; Alvord, E. C. Jr., In: *Experimental Allergic Encephalomyelitis: A Useful Model for Multiple Sclerosis* (Alvord, E. C., ed.), Liss, New York, 1984, pp. 1-511; Steinman, L., *Scientific American*, 269:106-114 (1993). The pathology of EAE is characterized by an influx of lymphocytes and monocytes into the brain and spinal cord with an associated demyelination of the central nervous system neurons (Raine, C S et al. *Lab Invest.* 43:150-157 (1980); Paterson, P Y et al., *Immunol. Rev.* 55:89-120 (1980)) resulting in partial or complete paralysis and in severe cases death. Neural antigen-specific $CD4^+$ T lymphocytes are the initiators of the response since in vivo depletion of $CD4^+$ T cells inhibits induction of EAE (Waldor, M K et al., *Science* 227:415-417 (1985). Only $CD4^+$ T cell lines or clones can passively transfer the disease (Holda, J A et al., *Europ. J. Immunol.* 12:453-455; Ben-Nun, A et al., *J. Immunol.* 129: 303-308). Thus, the disease may be characterized as being T lymphocyte-mediated and tissue-specific.

Compounds of the present invention which inhibit induction or pathogenesis of EAE are expected to be useful for treating MS or other cell-mediated diseases of the CNS, both in humans and in nonhuman mammals.

To study the effect of the present agents in vivo on a disease that includes in its pathogenesis the migration of T lymphocytes into a specific tissue, the brain, experiments were performed in the Lewis rat model of passively transferred EAE. MBP-specific T lymphocyte cell lines were generated from the draining LNs of Lewis rats that had been immunized with MBP in CFA essentially according to the method of Ben-Nun et al., 1981, supra.

Donor T lymphocytes were generated from female 10 to 12 week old Lewis rats weighing 150 to 200 g. These rats had been injected intradermally in each hind footpad with an emulsion of guinea pig MBP (gpMBP) prepared according to Deibler, G E et al., *Prepar. Biochem.* 2:139-165 (1972), incorporated herein by reference) in CFA (0.05 ml). The adjuvant emulsion was prepared by emulsifying equal volumes of a mixture of light mineral oil (Sigma) and a solution of the gpMBP in normal saline (0.5 mg/ml) and *Mycobacterium butyricum* (4 mg/ml; Difco). Thus, each rat received was 50 µg of MBP and 400 µg of *M. butyricum*. Approximately 11 days following injection the rats were euthanized and the draining LNs (popliteal and inguinal) were removed aseptically by blunt dissection and placed into lymphocyte culture medium as described above. A single cell suspension was prepared from the LNs as described above for spleen. The cells were washed twice in culture medium and any red blood cells were lysed with ammonium chloride as above.

These cells, at concentration of $5\times10^6$/ml were cultured for 72 hours in the presence of MBP (0.06 mg/ml) at 37° C. in a humidified atmosphere containing 7.5% carbon dioxide. The cells were collected and the lymphoblasts were isolated by centrifugation on a Ficoll (Pharmacia, Uppsala, Sweden) gradient in an identical manner to that described by Ben Nun et al. supra. The fraction containing ~90% lymphoblasts was cultured further in complete DMEM to which was added (15% v/v) a culture supernatant containing a mixture of growth factors (supernatant of concanavalin A-stimulated lymphocytes), 10% fetal calf serum, nonessential amino acids (Bio-Lab, Jerusalem, Israel). No antigen (MBP) was added. The cells were originally plated in 100 mm petri dishes at a concentration of $2\times10^5$ cells/mil and replated every 3 or 4 days. Prior to transfer into Lewis rat recipients, the cells were restimulated with antigen, MBP (0.01 mg/ml), and irradiated syngeneic thymocytes, as antigen-presenting cells, for 4 days. These cultured, stimulated T lymphocytes were highly encephalitogenic: as few as $5\times10^5$ cells could induced disease in naïve Lewis rats.

In a typical experiment, a group of 5 female Lewis rats, approximately 9 weeks old, weighing 110±15 grams was anesthetized with diethyl ether and implanted with mini-osmotic pumps (Alzet 2002, Alza Corp., Palo Alto Calif., USA) containing 1-(2,4,-diimethyl phenyl)-6-phosphono-mannoside dissolved in normal saline at a concentration that delivered the drug at a rate of 45 mg/kg/day. A second group of 5 control animals were implanted under anesthesia with a similar pump containing normal saline. Just prior to recovering from the anesthetic, each animal received $5\times10^5$ cells of the above encephalitogenic T cell line iv in 0.2 ml of normal saline. The results of this experiment appear in Table 4.

TABLE 4

Effect of Treatment with 1-(2,4,-dimethyl phenyl)-6-phosphono-mannoside on Passively Transferred EAE in Lewis Rats.

| Day | Saline Clinical Scores (individual rats) | | | | | Mean Score | Mannoside Clinical Scores (individual rats) | | | | | Mean Score |
|---|---|---|---|---|---|---|---|---|---|---|---|---|
| 4 | 1.5 | 1.5 | 1.5 | 1.5 | 2 | 1.6 | 0 | 0 | 0 | 0 | 0 | 0 |
| 5 | 2 | 2 | 2 | 2 | 2 | 2 | 0 | 0 | 1 | 1 | 1 | 0.6 |
| 6 | 2 | 2 | 2 | 2 | 2 | 2 | 0 | 0 | 1 | 2 | 2 | 1 |
| 7 | 2 | 0 | 0 | 1 | 1 | 0.8 | 0 | 0 | 1 | 0 | 1 | 0.4 |
| DI | | | 160 | | | | | | 40 | | | |

Disease severity was scored on an arbitrary scale of severity ranging from 0 to 5 as follows:
0, asymptomatic;
1, flaccid distal half of tail;
2, entire tail flaccid;
3, ataxia, difficulty in righting reflex;
4, hind limb weakness;
5, hind limb paralysis.
DI = Group Disease Index (see below)

All of the animals (5/5) in the control group developed clinical disease, whereas only 3/5 of the drug-treated animals developed disease. Moreover, in the drug-treated group, disease severity was lower than that observed in the controls, and disease onset was delayed. All of the control rats developed clinical symptoms of disease by day 4 whereas none of the drug treated rats had symptoms at this time.

All of the animals in the control group had maximum clinical scores for two consecutive days while none of the 3 drug treated animals that developed symptoms had maximum clinical scores for more than one day. The severity of EAE for each group of rats was calculated as a Disease Index (DI) which is (for those animals developing disease):

$$\frac{\text{mean of daily clinical score}}{\text{mean day of onset}^*} \times 100$$

This calculation allows a more complete assessment of the disease by incorporating both speed of onset and clinical severity and duration of the disease. Using this calculation, the control group had a DI of 160, whereas the treated group had a DI of 40.

In an identically designed experiment, rats were sacrificed on day 6 after T lymphocyte transfer and their spinal cords were harvested for histological assessment. Rats were deeply anesthetized (Nembutal) and perfused with 30 ml saline followed by 60 ml 10% neutral buffered formalin. Spinal cords were removed, fixed for 7 days in 10% formalin and embedded for sectioning. The lumbar-sacral spinal cord was transected and the halves embedded side by side for longitudinal sectioning. Six 5 µm sections were cut at various levels through the cord with 50 µm between levels. Sections were stained with hematoxylin and eosin and a minimum of 30 sections were counted at different levels in order to quantify the number of lesions.

The following results were obtained. The control group showed an extremely heavy lesion burden, on average approximately 15 lesions/section. In contrast, spinal cords from the drug treated group had an average of 3.5 lesions and no more than 8 lesions/section in the most affected animal.

EXAMPLE 6

Inhibition of Cell-Mediated Immune Disease of Synovial Tissue (Passively-Transferred Adjuvant Arthritis)

Passively transferred adjuvant arthritis (AA) is a T lymphocyte-mediated disease in which T cells from an animal with active arthritis are transferred to a naïve syngeneic recipient. The naïve recipient subsequently develops clinical signs of disease, including lymphocyte migration into the synovium with subsequent swelling of affected joints. The immunological nature of this disease and the dependence upon T lymphocytes has been well established for many years. See for example: Kayashima, K et al., 1978, *J. Immunol.* 120:1127-1131; Waksman, B H et al., 1963, *Int'l. Arch. Allergy* 23:129-139; Pearson, C M et al., 1964, *J. Exp. Med.* 120:547-560; Whitehouse, D J et al., 1969, *Nature* 224:1322.

The experiment in this Example was designed to study the effect of the agents of the present invention in vivo on a disease that requires T lymphocyte migration into a specific tissue (synovium). Male DA rats, 8 to 10 week old, were immunized with three 100 µl injections of CFA intradermally at the base of the tail. The CFA was prepared by mixing 8 mg/ml of *M. butyricum* (Difco Laboratories, USA) that had been ground to a fine powder using a mortar and pestle, in 85% light mineral oil (Sigma, USA) and 15% mannide monooleate (Sigma) and emulsifying this suspension, one part in one part saline. Thus, the final emulsion contained 4 mg/ml of *M. butyricum*.

Ten days after immunization, the rats were euthanized and their spleens removed aseptically. A single cell suspension in lymphocyte culture medium with 10% FCS was prepared as described above and adjusted to a concentration of 2×10⁶ cells/ml. Con A was added at a final concentration of 2 µg/ml. The cells were cultured at 37° C. in an atmosphere of 5% carbon dioxide for 72 hours.

Groups of 4 or 5 DA rats, 6 to 8 weeks of age were anesthetized with diethyl ether and implanted sc on the flank with Alzet 2002 ("2 week delivery") or Alzet 2001 ("1 week delivery") mini-osmotic pumps (Alza Corp., Palo Alto Calif., USA). One treatment group received 1-(2,4,-diimethyl phenyl)-6-phosphono-mannoside in the one week delivery Alzet 2001 mini-osmotic pumps. The drug was delivered at a dose of 25 mg/kg/day. The control group for this experiment received identical mini-osmotic pumps containing normal saline. In a second experiment another group of DA rats received 1-(2,4,-diimethyl phenyl)-6-phosphono-mannoside in the "2 week delivery" Alzet 2002 mini-osmotic pumps. This drug was delivered at a dose of 37 mg/kg/day. Control animals for this group received saline delivered in identical mini-osmotic pumps. While the animals were recovering from anesthesia, the above cultured lymphocytes which had been harvested and washed twice in HBSS were resuspended in normal saline and injected iv (lateral tai vein) into recipient rats, each of which received 75-90×10⁶ cells in 0.5 ml.

After 5 to 8 days, a characteristic thickening and cutaneous hyperemia of the distal joints of the hind legs became clinically apparent in saline treated control animals. Disease severity was evaluated and graded in each group by daily measurement of the mediolateral widths of both ankle joints. The data were expressed as the mean of the change (compared with width prior to cell injection) in mediolateral ankle width expressed in millimeters (±standard error of the mean).

Figure 1B:
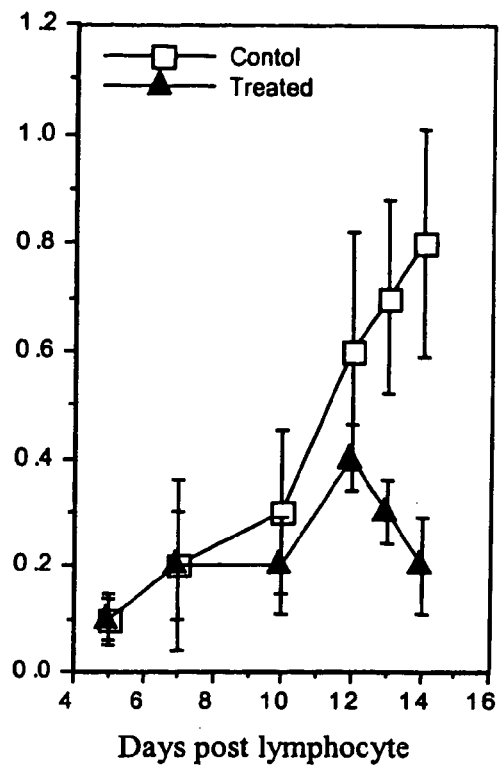

The compounds of the present invention delayed the onset of clinical signs and lessened the severity of the disease. FIG. 1 shows the results of a typical experiment in which 1-(2,4-dimethylphenyl)-6-phosphono-mannoside was delivered in the "one week delivery" Alzet 2001 mini-osmotic pumps at a dose of 25 mg/kg/day. At the end of the one week treatment period there was a highly statistically significant difference in the disease status of the treated versus the control animals. The control animals had severe swelling in the affected joints while the treated animals showed little swelling at the end of the treatment period.

FIG. 2 shows the results obtained of a typical experiment in which 1-(2,4,-dimethyl phenyl)-6-phosphono-mannoside was delivered in the "two week delivery" Alzet 2002 mini-osmotic pumps at a dose of 37 mg/kg/day. At the end of the two week treatment period, there was a highly statistically significant difference in the disease status of the treated versus the control animals. The control animals had severe swelling in the affected joints while the treated animals showed little swelling at the end of the treatment period.

EXAMPLE 7

Effect of Phosphono-Mannoside Derivatives in Various Models of Arthritis and Autoimmune Disease The compounds of the present invention are administered to rodents in several well known animal models of arthritis and autoimmune disease. These include adjuvant arthritis (see Example 6 above), streptococcal cell wall arthritis, *Mycoplasma arthritides* arthritis and collagen-induced arthritis. (See, for example, Pearson, C M, *Proc. Soc. Exp. Biol. Med.* 91:95 (1956); Cromartie, W J et al., *J. Exp. Med.* 146:1585 (1977); Trentham, D E et al., *J. Exp. Med.* 146:857 (1977); Chang, Y H et al., *Arthritis Rheum.* 23:62 (1980)).

I. Streptococcal Cell Wall Arthritis Model (See Schwab, J H et al., *J. Immunol.* 150:4151-4159 (1993))

A. Induction, Measurement, and Treatment of Arthritis

Female Lewis rats weighing about 175 g are injected intraarticularly (i.a.) under ether anesthesia above the calcaneus through the Achilles tendon into the tibiotalar (ankle) joint on day 0 with 2.0 µg of rhamnose equivalents (approximately 6.0 µg dry weight) of loop peptidoglycan-polysaccharide from cell wall of group A *Streptococci* (PG-APS) suspended in 10 µl of pyrogen-free saline, as described previously (Esser, R L et al., *Arthritis Rheum.* 28:1402 (1985); Stimpson, S A et al., In: *Pharmacological Methods in the Control of Inflammation,* Chang, J et al., Eds. Alan R. Liss, Inc., New York, p. 381 (1989)). Right or left joints are injected with PG-APS in alternate animals, and contralateral joints were injected with 10 µl of pyrogen-free saline.

The lateral diameter of the ankle joint is measured with a Fowler Ultra-Cal II digital caliper (Lux Scientific Instrument Corp., New York, N.Y.). The average of three measurements for each joint is recorded. Results are presented as the mean ±SE of the increase in joint diameter (difference between pre- and postreactivation).

B. Histopathology

Rats are sacrificed and the ankle joints are removed, skinned, fixed in formalin, decalcified, embedded in paraffin, sectioned sagitally, and stained with hematoxylin-eosin. The significance of differences between groups is assessed by Student's two tail t-test.

II. Adjuvant Arthritis (AA) Model (See, Especially, Chang et al., supra)

Male Lewis rats weighing 235-250 gm are used. Freund's complete adjuvant is either purchased commercially or prepared by grinding powdered *Mycobacterium butyricum* (10 mg; Difco Laboratories) with mineral oil (1.01 ml; Primol 355, Hampden Color Chemical Company). Adjuvant arthritis is produced by a single intradermal injection of the adjuvant into the tail or one hindpaw. The dose is about 0.5 mg heat killed *Mycobacterium tuberculosis* (Mt) suspended in 100 µl IFA. The volume of the uninjected hindpaw is measured by the method of Winter et al., *Proc. Soc. Exp. Biol Med.* 111:544 (1962) on day 0 and 16 (with respect to the injection of adjuvant). The increase in the volume of the uninjected hindpaw serves as a measure of arthritis.

To determine the effect of a therapeutic composition, rats are treated with either saline or the composition each day from day −1 to day −15 (with respect to adjuvant injection). The initial paw volume ($V_I$) is measured on the day of adjuvant injection. Sixteen days later, the volume ($V_F$) of the uninjected hindpaw is measured. Percent inhibition is calculated according to the following equation:

$$\% \text{ inhibition} = 1 - \frac{V_F \text{ drug} - V_I \text{ drug}}{V_F \text{ control} - V_I \text{ control}} \times 100$$

Alternatively, severity of arthritis is assessed by scoring each paw from 0 to 4 based on degree of swelling, erythema, and deformity of the joints. Thus the maximum possible arthritis score is 16.

III. Collagen Type II-Induced Arthritis (CIA) Model (see Trentham et al., supra)

Sensitization Procedures. Collagen is dissolved in 0.1M acetic acid at a concentration of 1 mg/ml. Equal volumes of collagen solution and CFA or IFA are mixed and emulsified. One ml of the cold emulsion is immediately injected intradermally in four to six sites on the backs of the rats. Small ulcers frequently form at the injection site, but these heal without sequelae in 7-10 days. Control injections consist of (a) acetic acid emulsified in CFA or IFA or (b) human or chick type II collagen dissolved in acetic acid and injected intradermally without adjuvant. As an additional control, 1.0 ml of $MgCl_2$-extractable cartilage proteoglycans containing approximately 200 µg uronate per ml is mixed with 0.5 ml of CFA or IFA, emulsified, and injected as with collagens.

Unless otherwise specified, booster doses consisting of 0.5 mg collagen dissolved in 0.5 ml 0.1 M acetic acid are given ip without adjuvant 21 days after primary immunization. One ml of the $MgCl_2$ extract is given ip after an identical interval to the proteoglycan control animals. Adjuvant arthritis is induced by intradermal injection of 0.1 ml CFA H37 at the base of the tail.

Arthritis Evaluation. Animals are observed daily for the onset of arthritis, and an arthritic index is derived by grading the severity of involvement of each paw from 0 to 4. Scoring is based on the degree of periarticular erythema and edema as well as deformity of the joints (Wood, F D et al., *Int. Arch. Allergy Appl. Immunol.* 35:456 (1969)). Swelling of hindpaws is also quantitated by measuring the thickness of the ankle from medial to lateral malleolus.

IV. Autoimmune Model MRL/lpr Mice (See: Kim, C. et al., *J. Exp. Med.* 174:1431-1437 (1991))

MRL/Mp-lpr/lpr mice (4-6 wks old) are purchased from the Jackson Laboratory (Bar Harbor, Me.) or other supplier.

Enzyme Immunoassay (EIA) for Anti-DNA Antibodies and Immune Complexes

Polystyrene microtiter wells are coated with double-stranded DNA (ds-DNA) or goat C1q. Blood is obtained from individual mice before the biweekly injections. Sera are diluted in 0.05% Tween-20 in PBS at a 1:500 dilution and allowed to incubate in the plates for 60 min at room temperature. The plates are then washed with PBS-Tween, and 50 µl of 1/1000 dilutions of goat anti-mouse IgG and IgM antibodies conjugated to urease (or another enzyme that is known to be useful in EIA) are added to the plates. After incubation for 30 min., the plates are washed three times with PBS-Tween and twice with 0.15M NaCl. The plates are then incubated with a solution of the chromogenic substrate for the enzyme. Colorimetric change is quantified by measuring absorbance at the appropriate wavelength for the particular colored product of the enzymatic reaction using a microplate reader.

Proteinuria and Physical Symptoms

Urine is obtained from mice. Protein concentration and the presence of blood in urine is measured semiquantitatively by commercial reagent strips for urinalysis.

Physical symptoms are visually scored as: 0, no symptoms; 0.5, trace; 1-4, when visible symptoms are observed, with 4 being the most severe (physical symptoms include lymphadenomegaly, immune complex vasculitis, and necrosis of the ears). Scores representing physical symptoms are calculated by determining the total score for each group and then dividing by the number of animals alive in that group when the measurement is taken.

Treatment

For each of the models described above, treatment is started 6-14 days after the injection of the inducing agents (or in the case of MRL/lpr mice beginning at 4 weeks of age). Doses vary from 1 µg to 100 mg of the following compounds:

1-(2,4,-dimethyl phenyl)-6-phosphono-mannoside;

1-(2,4,6-trimethyl phenyl)-6-phosphono-mannoside;

1-(2-methyl,4-chlorophenyl)-6-phosphono-mannoside;

1-(2-methyl,4-fluorphenyl)-6-phosphono-mannoside;

1-(2-methyl,4-trifluoromethylphenyl)-6-phosphono-mannoside;

1-(2-methyl,4-trifluoromethyl -6-phosphono-mannoside or any other of the novel T cell migration-inhibitory compounds of the present invention.

The compounds are administered iv or ip at 1 week intervals for 4 weeks. Outcomes are assessed as described above. For all arthritis models outcome measures include:

(a) quantitative measurement and grading of joint swelling erythema or deformity, and
(b) assessment of histopathology of joints using a quantitative grading system.

In all the models described, the four compounds listed above are effective in significantly reducing direct or indirect measures of arthritis.

EXAMPLE 8

Phosphono-Mannoside Derivatives in the Treatment of Rheumatoid Arthritis in Humans (See: Koopman, W J (ed)*Arthritis and Allied Conditions: A Textbook of Rheumatology*, Lippincott, Williams & Wilkins; 13th edition, 1996.)

Treatment Procedure

Doses of the compounds of this invention are determined as described above using, inter alia, appropriate animal models of autoimmune disease.

A treatment consists of injecting a patient with 0.1, 1, 10 or 100 mg of the compound iv, or infusing the compound in 100 ml of normal saline over a 30 minute period twice weekly at three day intervals for six weeks. Clinical responses are assessed by the criteria described below. Treatments are continued in patients with stable or exacerbating disease. Treatment is generally given on an outpatient basis.

Clinical Outcome Measures

Outcome measures used to assess treatment efficacy in RA should detect the smallest clinically important change and, at the same time, be reliable and valid with respect to capturing the dimensionality of the clinical and pathophysiologic responses. To avoid bias, both patients and assessors preferably are blinded during testing.

The methods most commonly used are based on quantitation of cardinal features: pain, swelling, heat and redness. Laboratory tests may also be used in assessment, though a treatment that only reduces a laboratory measure without, for example, relieving joint pain is of less interest. No single ideal method is known to accurately reflect disease activity in arthritis. As a result, it is useful to aggregate end points into a composite index. Composite indices are constructed by statistical or judgmental procedures that allow aggregation of scores assigned to different end points.

Objective and sensitive measurements are preferred to subjective ones. One sensitive parameter to change with antirheumatic drug therapy in RA is the patient's subject assessment of pain relief. Objective measurements include radionuclide joint uptake. Others are the 50-foot walking time and assessment of functional disability (the second most important symptom in osteoarthritis). Examples of useful outcome measures appear in Table 5, below.

TABLE 5

Outcome Measures for Clinical Trials in Arthritis
Altman, R. D. et al., Clin. Rheum. Dis. 9: 681–693 (1983)

FDA Guidelines (1977)

Joint swelling
Joint redness
Tenderness on pressure
Pain at rest or on motion
Range of motion
50-foot walking time TABLE 5-continued Outcome Measures for Clinical Trials in Arthritis
Altman, R. D. et al., Clin. Rheum. Dis. 9: 681–693 (1983)

Clinician's global assessment
Patient's global assessment
Altman et al. (supra)

Pain (using visual analogue scales)
Tenderness on pressure/motion
Clinician's global assessment of current status and degree of change in status
Patient's global assessment of current status and degree of change in status
50-foot walking time (for patients with hip/knee involvement)
Grip strength (for patients with hand involvement)
Bellamy and Buchanan
Clin. Rheumatol. 3: 293–305 (1984)

Pain
Patient global assessment
Range of movement
Physician global assessment
Joint stiffness
Qualitative aspects of sleep
Walking time
Activities of daily living
Joint tenderness
Analgesic compound
Joint swelling
Signal joints
Ascent time
Muscle power**
Hand function
Radiology
Joint temperature Because pain is the major complaint of the rheumatic sufferer, measurement of pain relief is important in assessing clinical response to the therapeutic composition or method of this invention. Adjectival scales may be used with numeric values given to the adjectival scale, for example: 0=no pain, 1=slight pain, 2=moderate pain, 3=severe pain, and 4=extremely severe or agonizing pain. Such a scale is known to discriminate between nonsteroidal anti-inflammatory analgesics and placebo in short-term trials (Lee, P., *J. Rheumatol* 3:283-294 (1976)). Other methods of measuring pain include assessment of pain threshold and pain tolerance (Huskisson, E C, *Clin. Rheum. Dis.* 2:37-49(1976)).

To score joint tenderness, firm digital pressure is applied to the joint margins and the degree of tenderness is graded by the patient's response. Lansbury's Articular Index (Lansbury, J, *Arthritis Rheum.* 1:505-522 (1958)) is useful in assessing progress. A simple count of clinically active joints, as determined by pain on passive motion, tenderness on pressure, or inflammatory joint swelling is used (Cooperat. Clin. Comm. Amer. Rheum. Assoc., *Clin. Pharmacol. Ther.* 8:11-38 (1967)). Scoring a few selected "signal" joints may permit better assessment of therapeutic effect than a total joint count. A standardized dolorimeter tested against the Lansbury indices is highly reproducible. The Ritchie Articular Index (RAI) is based on summation of joint responses after firm digital pressure. The responses are recorded as 0=no tenderness, +1=patient says it is tender, +2=patient says it is tender and winces, and +3=patient says it is tender, winces, and withdraws limb. The sum of this Index is 78 and reflects exacerbations of disease and improvement induced by antirheumatic drugs. This index correlates with the patient's assessment of pain, in the upper limbs with grip strength, and in the lower limbs with the time to walk 50 feet.

Various instruments are available to measure grip strength which is determined by the strength of the muscles in the forearm and hand, and the pain and degree of joint destruction in the wrist, hand, and finger joints; grip strength correlates with the RAI.

The range of motion of peripheral joints in normal subjects is known, and these measures have been assessed in studies of ankylosing spondylitis. Spinal movement is measured by several methods including the Dunham spondylometer (Anderson, J, *Clin. Rheum. Dis.* 8:631-653 (1982)), skin distraction (Moll, J et al., *Rheum. Phys. Med.* 11:293-312 (1972)), an inclinometer (Domjan, L et al., *Hung. Rheum.* 28 (Suppl):71-76 (1987)). Timing of certain movements or set maneuvers related to activities of daily living, are useful, in particular the time to walk 50 feet (Lee, supra; Grace, E M et al., *Br. J. Rheumatol.* 27:372-374 (1988)).

Increase in warmth of overlying skin is a cardinal feature of inflammation and can be measured in various ways (e.g., Bacon, P. A. et al., *Clin. Rheum. Dis.* 2:51-65 (1976)). Infrared quantitative thermography shows reproducible changes in disease activity and is useful in assessing efficacy of a treatment composition or method. Thermography provides a noninvasive, reproducible, sensitive, and quantifiable method of assessing improvement in joint inflammation (Ingpen, M L, *Ann. Phys. Med.* 9:322-327 (1968)).

Laboratory Tests

Certain laboratory tests reflect the severity of joint inflammation and may be used to monitor the efficacy of the therapeutic compositions and methods of this invention. The most frequently used test is the erythrocyte sedimentation rate (ESR). Other measures used include evaluation of various acute-phase reactants, such as C-reactive protein, haptoglobin, fibrinogen, α-2 macroglobulin, and plasma viscosity (McConkey, B et al., *Q. J. Med., New Series* 41:115-125 (1972); McConkey, B et al., *Q. J. Med., New Series* 42:785-791 (1973); Constable, T J et al., *Lancet* 1:1176-1179 (1975); Crook, L et al., *Ann. Clin. Lab. Sci.* 10:368-376 (1980); Dixon, J A et al., *Scand. J. Rheumatol.* 13:39-44 (1984); Cockel, R et al., *Ann. Rheum. Dis.* 30:166-170 (1971)); titer of IgM rheumatoid factor or of immune complexes (Pope, R M et al., *Ann. Rheum. Dis.* 45:183-189 (1986); Reeback J S et al, *Ann. Rheum. Dis.* 44:79-82 (1986); Reynolds, W J et al., *J. Rheumatol.* 13:700-706 (1986)); tests of lymphocyte function (Reynolds, W J et al., *J. Rheumatol.* 13:700-706 (1986); Alepa, F P et at., *Arthritis Rheum.* 13:754-760 (1970); Swanson, M A et al., *N. Engl. J. Med.* 277:163-170 (1967)); displacement of L-tryptophan from serum albumin; serum iron concentration (Cockel, supra), eosinophilia, thrombocytosis (Hutchinson, R M et al., *Ann. Rheum. Dis.* 35:138-142 (1976)); serum concentrations of sulfhydryl groups (Lorber, A et al., *Metabolism* 20:446-455 (1971)); serum copper concentrations (Brown, D H et al., *Ann. Rheum. Dis.* 38:174-176 (1979)); serum propeptide levels (Horsley-Petersen et al., *Rheum.* 29:592-599 (1986)); synovial fluid analysis (Hall, S H et al., *Ann. Rheum. Dis.* 37:351-356 (1978)).

Various methods are used to score radiologic changes in rheumatoid arthritis, the most useful of which are count erosions and assessment of joint space narrowing. Radionuclides can also be used to quantify joint inflammation (Dick, W C, *Semin. Arthritis Rheum.* 1:301-325 (1972); Wallace, D J et al., *Arthritis Rheum.* 11:172-176 (1981)). These are administered intra-articularly and the rate of clearance from the joint determined or, alternatively, they are administered iv and the rate of accumulation over a joint (or joints) measured. The clearance of $^{133}$Xe after intra-articular injection provides an indirect measurement of synovial blood flow. $^{99m}$TcO$_4$ is also used. Radionuclide joint uptake in both large and small joints is known to be reduced with successful anti-rheumatic therapeutics such as NSAIDs, corticosteroids, gold or D-penicillamine.

Results: 375 patients with RA are treated with one of five compounds (75/group):
(1) 1-(2,4,-dimethyl phenyl)-6-phosphono-mannoside;
(2) 1-(2,4,6-trimethyl phenyl)-6-phosphono-mannoside;
(3) 1-(2-methyl,4-chlorophenyl)-6-phosphono-mannoside;
(4) 1-(2-methyl,4-fluorphenyl)-6-phosphono-mannoside;
(5) 1-(2-methyl,4-trifluoromethyl)-6-phosphono-mannoside;

According to the 8 measures listed under "FDA Guidelines" in Table 5, above, >75% of the patients treated with any of the above compounds show significant cumulative improvement across all measures.

Toxicity

The incidence of side effects (as % of total treatments across groups) are as follows: chills—10; fever—10; pain—5; nausea—5; respiratory—3; headache—3; tachycardia—2; vomiting—2; hypertension—2; hypotension—2; joint pain—2; rash—2; flushing—1; diarrhea—1; itching/hives—1; bloody nose—1; dizziness—<1; cramps—<1; fatigue—<1; feeling faint—<1; twitching—<1; blurred vision—<1; gastritis<1; redness on hand—<1. Other minor changes observed are clinically insignificant.

All the references cited above are incorporated herein by reference in their entirety, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

The invention claimed is:

1. A compound of formula I:

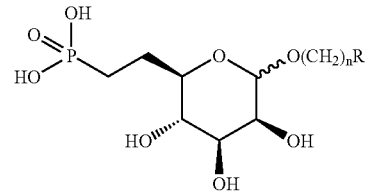

Formula I or a salt thereof;
wherein n is an integer from 0 to 3,
the —O(CH$_2$)$_n$R group is in an axial or equatorial position, and
R is optionally substituted heteroaryl or optionally substituted aryl wherein the substituent is selected from the group consisting of —Cl, —F, —CF$_3$, —CH$_3$, —CH$_2$CH$_3$, —(CH$_2$)$_m$CO$_2$R$^1$, —(CH$_2$)$_m$OR$^2$, (CH$_2$)$_m$CONR$^2$R$^3$, and —(CH)$_m$NR$^1$R$^1$,
wherein m is an integer from 0 to 3;
R$^1$ is selected from the group consisting of H, alkyl and aryl; and
R$^2$ and R$^3$ are independently selected from the group consisting of H, alkyl, aryl and acyl, wherein when n=0, R is not 4-aminophenyl.

2. The compound of claim 1, wherein, when n=0, R is not an amino substituted phenyl.

3. The compound of claim 1, wherein, when n=0, R is not an amino substituted aryl.

4. The compound of claim 1, wherein R is not 4-aminophenyl.

5. The compound of claim 1, wherein, R is not an amino substituted phenyl.

6. The compound of claim 1, wherein, R is not an amino substituted aryl.

7. The compound of claim 1 wherein R is selected from the group consisting of phenyl; 2-methylphenyl; 2,4-dimethylphenyl; 2,4,6-trimethylphenyl; 2-methyl-4-chlorophenyl; 2-methyl-4-fluorophenyl; 2,3 or 4-methoxyphenyl; 2,3 or 4-trimethoxyphenyl; 2,3 or 4-methylphenyl; 2-methoxy-4-methylphenyl; 2-methyl-4-methoxyphenyl; 2-trifluoromethoxy-4-methylphenyl; 2-methyl-4-trifluoromethoxyphenyl; 2,3 or 4-pyridyl; 2,4 or 5-pyrimidinyl; 2 or 3-thiophenyl; 2,4, or 5-(1,3)-oxazolyl; 2,4 or 5-(1,3)-thiazolyl; 2 or 4-imidazolyl; and 3 or 5-symtriazolyl.

8. The compound of claim 7 wherein R is selected from the group consisting of 2,4-dimethylphenyl, 2,4,6-trimethylphenyl, 2-methyl,4-chlorophenyl; 2-methyl, 4-fluorophenyl.

9. The compound of claim 8, wherein the compound is 1-(2,4-dimethylphenyl)-6-phosphono-mannoside.

10. The compound of claim 8, wherein the compound is 1-(2,4,6-trimethylphenyl)-6-phosphono-mannoside.

11. The compound of claim 8, wherein the compound is 1-(2-methyl,4-chlorophenyl)-6-phosphono-maunoside.

12. The compound of claim 8, wherein the compound is 1-(2-methyl,4-fluorphenyl)-6-phosphono-mannoside.

13. The compound of claim 1, wherein the compound is 1-(2-methyl, 4-trifluoromethyl)-6-phosphono-mannoside.

14. A pharmaceutical composition comprising:
    (a) the compound or salt of claim 1; and
    (b) a pharmaceutically acceptable carrier, diluent or excipient.

15. A method of inhibiting T lymphocyte migration from blood to a tissue or other extravascular site in a subject, comprising administering to the subject an effective amount of the compound of claim 1 or a pharmaceutically acceptable salt, derivative or prodrug thereof.

16. A method of inhibiting T lymphocyte migration from blood to a tissue or other extravascular site in a subject, comprising administering to the subject an effective amount of the pharmaceutical composition of claim 14.

17. The method of claim 15 where the T lymphocyte migration is associated with a disease or condition in which migrating T lymphocytes mediate an undesired inflammatory or immune response in the tissue or extravascular site.

18. The method of claim 16. where the T lymphocyte migration is associated with a disease or condition in which migrating T lymphocytes mediate an undesired inflammatory or immune response in the tissue or extravascular site.

19. A method of treating arthritis or multiple sclerosis in a subject in need thereof, comprising administering to the subject an effective amount of the compound of claim 1 or a pharmaceutically acceptable salt thereof, wherein said compound or salt causes an inhibition of T lymphocyte migration.

20. A method of treating arthritis or multiple sclerosis in a subject in need thereof, comprising administering to the subject an effective amount of the pharmaceutical composition of claim 14, wherein said composition causes an inhibition of T lymphocyte migration.

* * * * *

UNITED STATES PATENT AND TRADEMARK OFFICE
CERTIFICATE OF CORRECTION

PATENT NO. : 7,648,966 B2  Page 1 of 1
APPLICATION NO. : 10/557773
DATED : January 19, 2010
INVENTOR(S) : Cowden et al.

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 385 days Delete the phrase "by 385 days" and insert -- by 719 days --

Column 39, line 28, "maunoside" should be changed to -- mannoside --.

Signed and Sealed this

Twenty-seventh Day of July, 2010

David J. Kappos
*Director of the United States Patent and Trademark Office*